United States Patent
Menon et al.

(10) Patent No.: US 12,097,315 B2
(45) Date of Patent: Sep. 24, 2024

(54) CARDIAC DRAINAGE CANNULA AND RELATED METHODS AND SYSTEMS

(71) Applicant: Berlin Heart GmbH, Berlin (DE)

(72) Inventors: Ares K. Menon, Berlin (DE); Kevin T. Fischer, The Woodlands, TX (US)

(73) Assignee: Berlin Heart GmbH, Berlin (DE)

( * ) Notice: Subject to any disclaimer, the term of this patent is extended or adjusted under 35 U.S.C. 154(b) by 1385 days.

(21) Appl. No.: 16/453,541

(22) Filed: Jun. 26, 2019

(65) Prior Publication Data
US 2020/0405943 A1 Dec. 31, 2020

(51) Int. Cl.
*A61M 1/36* (2006.01)
*A61B 17/34* (2006.01)
(Continued)

(52) U.S. Cl.
CPC ....... *A61M 1/3659* (2014.02); *A61B 17/3468* (2013.01); *A61M 1/32* (2013.01);
(Continued)

(58) Field of Classification Search
CPC .... A61M 1/3659; A61M 1/3667; A61M 1/32; A61M 1/3639; A61M 60/531; A61M 60/38; A61M 60/532; A61M 60/113; A61M 60/857; A61M 2202/0413; A61M 2205/04; A61M 2205/3331; A61M 2210/125; A61M 2230/30; A61B 17/3468
See application file for complete search history.

(56) References Cited

U.S. PATENT DOCUMENTS

| | | | | |
|---|---|---|---|---|
| 5,769,812 A | * | 6/1998 | Stevens | A61M 1/3653 604/509 |
| 6,241,699 B1 | * | 6/2001 | Suresh | A61M 60/497 604/7 |

(Continued)

FOREIGN PATENT DOCUMENTS

| CN | 107073193 A | 8/2017 |
|---|---|---|
| WO | WO 00/57805 | 10/2000 |

(Continued)

OTHER PUBLICATIONS

Mihoko Hashimoto et al., "Incorporating a Pressure Sensor-Transmitter (RF) Complex on Transseptal Cannula for use with TandemHeart™ PTVA System," dated Dec. 5, 2003, pp. 1-20, published by University of Pittsburgh, Pittsburgh, Pennsylvania.

(Continued)

*Primary Examiner* — Philip R Wiest
(74) *Attorney, Agent, or Firm* — Crowell & Moring

(57) ABSTRACT

The disclosure provides a method of placing a cardiac drainage cannula into a patient's heart. In some embodiments, the method comprises the steps of (a) inserting the cannula percutaneously into an internal jugular vein, (b) advancing the cannula through the internal jugular vein and into the right atrium of the heart, and (c) advancing the cannula through the atrial septum into the left atrium of the heart. Further aspects of the disclosure provide a method of draining blood from the left atrium or left ventricle of a patient's heart using a cardiac drainage cannula. The disclosure also provides a cardiac drainage cannula and a mechanical circulatory support system.

25 Claims, 8 Drawing Sheets

(51) Int. Cl.
   *A61M 1/32*      (2006.01)
   *A61M 60/113*    (2021.01)
   *A61M 60/38*     (2021.01)
   *A61M 60/531*    (2021.01)
   *A61M 60/562*    (2021.01)
   *A61M 60/857*    (2021.01)

(52) U.S. Cl.
   CPC ........ *A61M 1/3639* (2013.01); *A61M 1/3667* (2014.02); *A61M 60/113* (2021.01); *A61M 60/38* (2021.01); *A61M 60/531* (2021.01); *A61M 60/562* (2021.01); *A61M 60/857* (2021.01); *A61M 2202/0413* (2013.01); *A61M 2205/04* (2013.01); *A61M 2205/3331* (2013.01); *A61M 2210/125* (2013.01); *A61M 2230/30* (2013.01)

(56) References Cited

U.S. PATENT DOCUMENTS

| | | | | |
|---|---|---|---|---|
| 2004/0191116 | A1* | 9/2004 | Jarvik | A61M 60/806 604/6.11 |
| 2005/0154250 | A1* | 7/2005 | Aboul-Hosn | A61M 60/148 600/16 |
| 2006/0063965 | A1* | 3/2006 | Aboul-Hosn | A61M 25/0043 600/16 |
| 2007/0161845 | A1* | 7/2007 | Magovern | A61M 60/585 600/16 |
| 2007/0282243 | A1* | 12/2007 | Pini | A61M 60/35 604/6.14 |
| 2013/0158338 | A1* | 6/2013 | Kelly | A61M 25/007 600/16 |
| 2016/0022896 | A1* | 1/2016 | Burkhoff | A61M 1/3621 600/17 |

FOREIGN PATENT DOCUMENTS

| | | |
|---|---|---|
| WO | WO 2005/037345 A2 | 4/2005 |
| WO | WO 2018/073399 A1 | 4/2018 |

OTHER PUBLICATIONS

International Search Report and Written Opinion regarding PCT/EP2020/067965 dated Oct. 29, 2020, 17 pages.

First Office Action received for China Application No. 202080046267.8 issued Oct. 9, 2023 (with English translation) (18 pages).

* cited by examiner

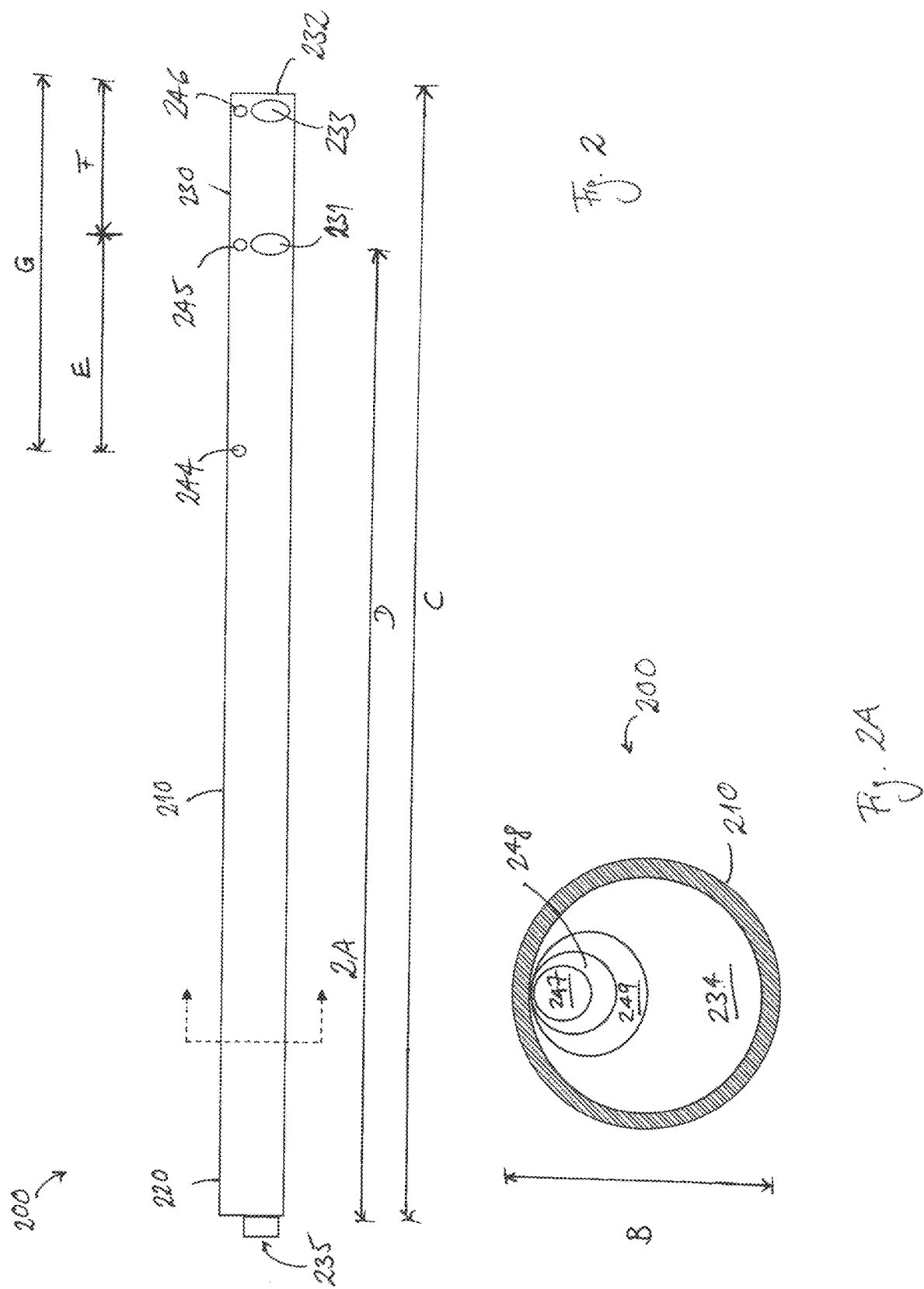

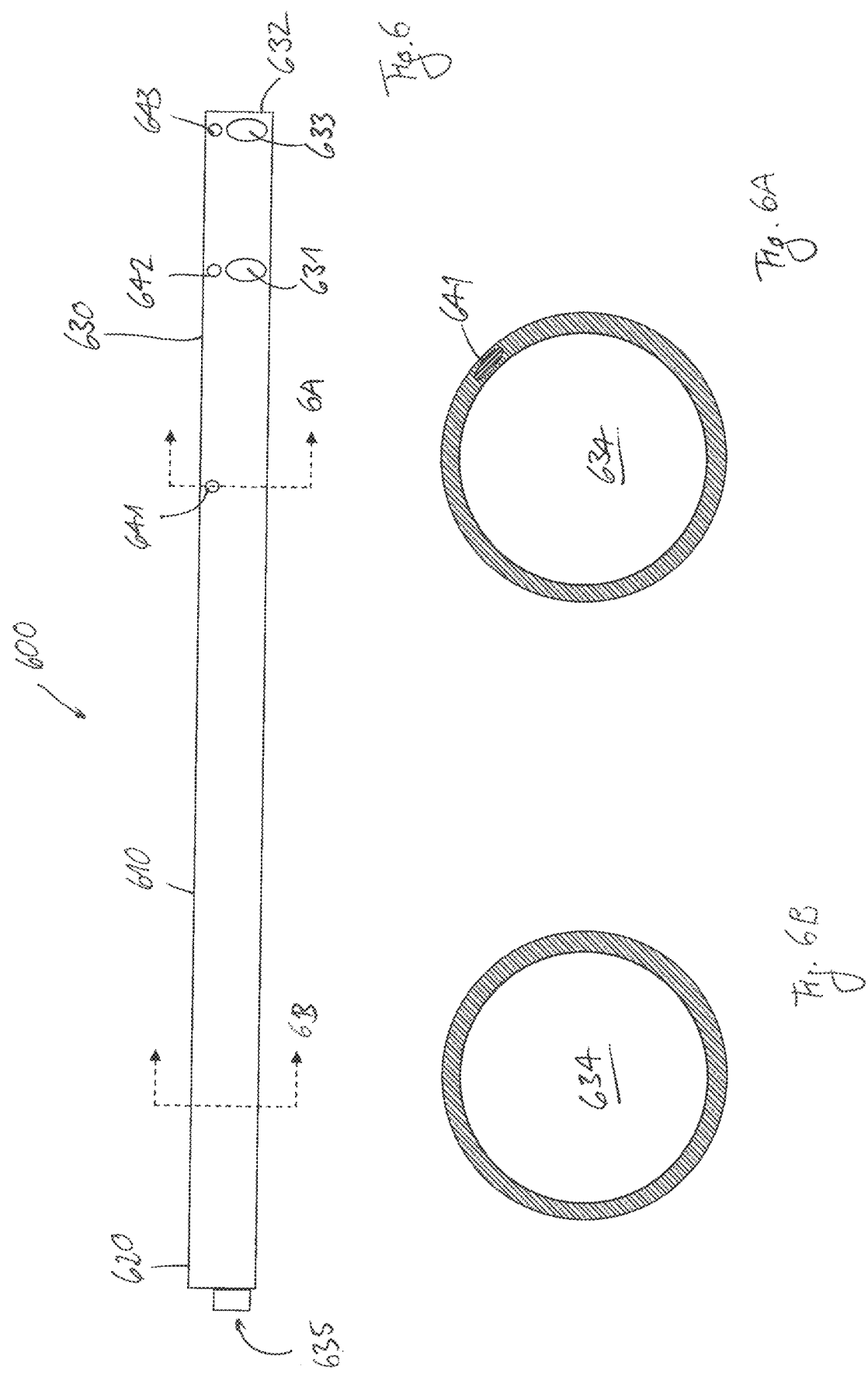

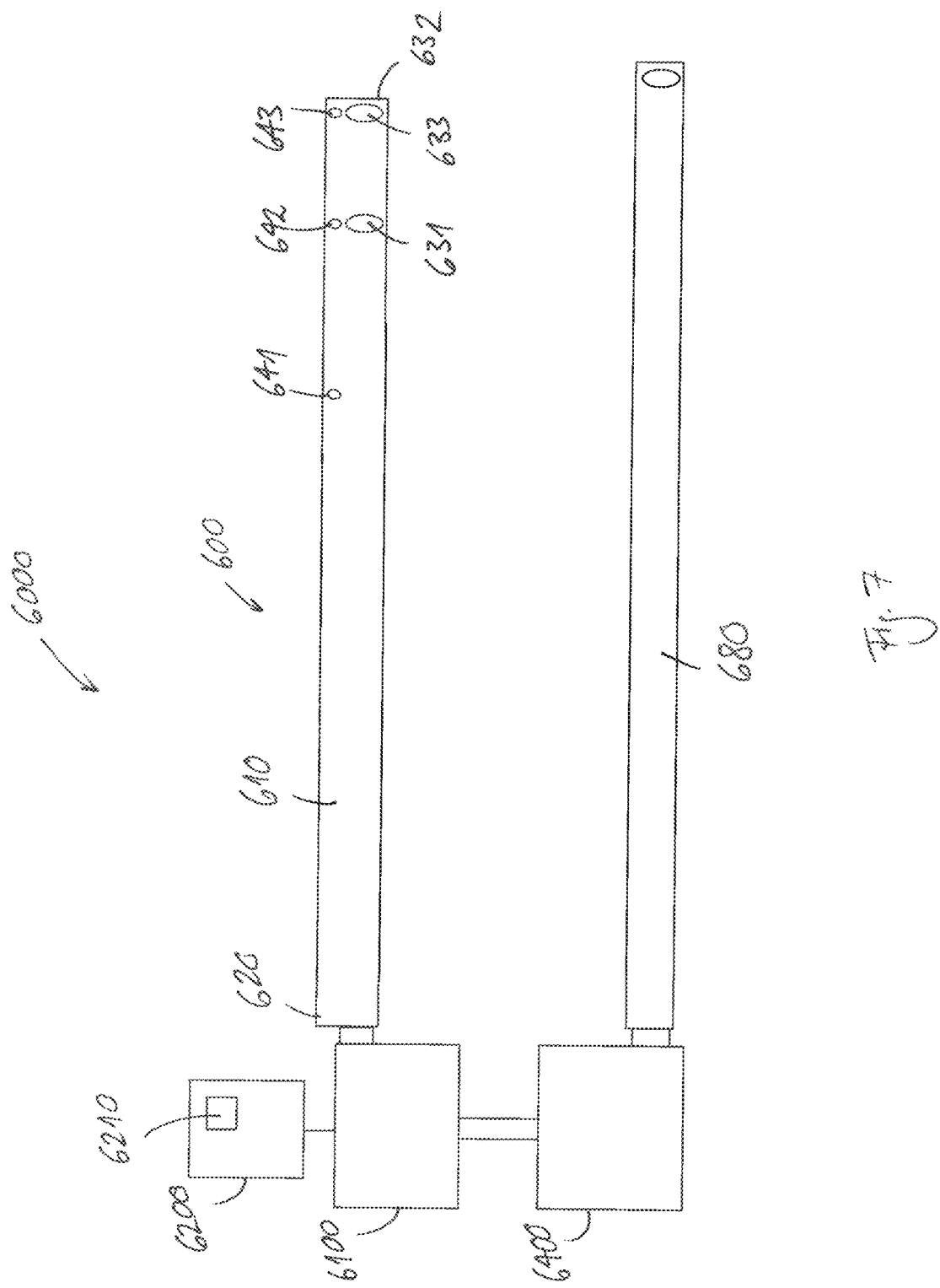

CARDIAC DRAINAGE CANNULA AND RELATED METHODS AND SYSTEMS

TECHNICAL FIELD

The present disclosure generally relates to a cardiac drainage cannulas and related methods and systems. Some aspects relate to a method of placing a cardiac drainage cannula into a patient's heart, more particularly, a method of placing a cardiac cannula into a left atrium or left ventricle of a patient's heart. Some aspects relate to a method of draining blood from the left atrium or left ventricle of a patient's heart using a cardiac drainage cannula. Furthermore, some aspects relate to a mechanical circulatory support system for providing hemodynamic support to a patient by augmenting or supplementing the blood flow through the circulatory system of a patient.

BACKGROUND ART

A cardiac drainage cannula, as part of a mechanical circulatory support system, may be used for draining blood from a patient's heart and for delivering the drained blood to extracorporeal components of the system, such as to an extracorporeal blood pump and/or an extracorporeal oxygenation device. An example of a mechanical circulatory support system is offered by Livallova PLC under the mark of TandemHeart®. The system includes an extracorporeal blood pump, a cardiac drainage cannula, a perfusions cannula, and further system components. The cardiac drainage cannula is usually sized and configured to be inserted into the femoral vein and advanced towards the heart into the right atrium. The distal end is advanced transseptally into the left atrium. A proximal end of the drainage cannula remains outside the patient's body and is connected to the system's extracorporeal blood pump.

During operation of the system, blood is drained from the left atrium through the drainage cannula and delivered to the pump and returned back into the body, for instance, via an arterial perfusion cannula into the femoral artery. Draining blood from the left atrium of the heart may help, for instance, to decompress and rest the left ventricle of the heart, in order to support recovery of the heart, particularly in cases of heart failure or congestive heart failure.

Potential complications associated with mechanical cardiac support systems and methods may include, among others, thrombosis and infections, particularly at access sites of the drainage cannula and the perfusion cannula. Furthermore, setting up the mechanical support system and connecting it to the patient's circulatory system can be challenging and may take precious time, particularly in emergency situations. In addition, the installed and operating system, particularly the drainage and perfusion cannulas, may degrade the patient's mobility. Further challenges are related to the operation and control of the running system. Particularly, the pump may need to be controlled in a manner to provide adequate circulatory support to the patient. On the one hand, it may be one goal to effectively alleviate workload from the left ventricle of the heart which requires a sufficient drainage rate and pump speed. On the other hand, a too high drainage rate and pump rate may increase the risk of emptying of the left atrium and of suction. Furthermore, in addition to the risk of left ventricular failure, there may also be an elevated risk of right ventricular failure when providing left ventricular support.

The present disclosure therefore aims at alleviating one or more of the problems and challenges described above.

SUMMARY

In one aspect, the disclosure relates to a method of placing a cannula, more particularly a cardiac drainage cannula, within a left atrium of a heart in a living body. In some embodiments, the method may comprise the steps of: (a) inserting the cannula percutaneously into an internal jugular vein of the body, (b) advancing the cannula through the internal jugular vein and into the right atrium of the heart, and (c) advancing the cannula through the atrial septum into the left atrium of the heart and, optionally, through the mitral valve further into the left ventricle of the heart. A proximal end portion of the cannula may remain outside of the body. Examples of dimensions (e.g. outer diameter and insertable length) are provided further below. Typically, the inserted length of a drainage cannula that is inserted via the internal jugular vein is much smaller then the inserted length of a drainage cannula that is inserted via the femoral vein, for instance. As a result, as there is a smaller surface area of the cannula in direct contact with the blood of the patient, the risk is of thrombosis is significantly reduced. Furthermore, the mobility of the patient is improved.

In some embodiments, step (a) may include advancing the cannula through a percutaneous puncture which extends from an outer skin surface (e.g., on the patient's neck) through the skin, through tissue between skin and internal jugular vein, and through a wall of internal jugular vein. The percutaneous puncture may be performed, for instance, by means of a needle (e.g. a trocar) and without incising tissue and without using a scalpel or similar cutting tool. Accordingly, in some embodiments, the method may comprise puncturing the skin with the needle and advancing the needle through the skin and towards the internal jugular vein, and puncturing a wall of the internal jugular vein. Optionally, before inserting the cannula, a dilatator may be inserted into the percutaneous puncture in order to enlarge the puncture. Only optionally, a scalpel may be used to further enlarge the puncture in order to facilitate advancing the dilatator. Assessing the internal jugular vein by means of a puncture has the further advantage that it can be performed very fast, saving precious time particularly in emergency situations.

In some embodiments, step (b) may include advancing the cannula through the right internal jugular vein (vena jugularis interna), into and through the right brachiocephalic vein, into and through the superior vena cava, and into and through the right atrium.

In some embodiments, the method may be performed by employing the Seldinger technique. The needle used for forming the percutaneous puncture may then have a lumen (e.g., a trocar). A guidewire with pigtail, for instance, may be inserted through the lumen of the needle into the lumen of internal jugular vein. The needle may subsequently be removed, keeping the guidewire in place. The guidewire may be advanced along the path described above, i.e., through the right internal jugular vein, into and through the right brachiocephalic vein, into and through the superior vena cava, and into the right atrium.

In some embodiments, the method typically comprises performing an atrial septostomy which includes puncturing the atrial septum using a sharp instrument to form a transseptal puncture (hole). The transseptal puncture may be formed, for instance, at an area of the fossa ovalis. The sharp instrument used for puncturing the atrial septum may be, for instance, a transseptal needle, such as a Brockenbrough needle. In some embodiments, the atrial septostomy may include passing a sheath (e.g. a Mullins sheath) over the aforementioned guidewire into the right atrium. The sharp instrument may then be inserted and advanced through the sheath to the atrial septum to perform the transseptal puncture. The guidewire may be advanced through the transseptal puncture. A dilatator, e.g. Mullin Mandrin, may be advanced over the guidewire though the transseptal puncture to enlarge the transseptal puncture. The sharp instrument, the sheath and the dilatator used for the atrial septostomy are removed after use, keeping the guidewire in place.

The atrial septostomy is typically performed before the percutaneous insertion of the cannula. The cannula may then be inserted percutaneously and advanced along the guidewire through the transseptal puncture into left atrium and, optionally, through the mitral valve into the left ventricle.

In some embodiments, the step (c) may further comprise advancing the cannula from the left atrium through the mitral valve of the heart into the left ventricle of the heart.

In some embodiments, the method may further comprise fixating the cannula to a skin portion adjacent to a percutaneous insertion site of the cannula which may include, for instance, forming a suture connecting the cannula to the skin portion. As described further below, the cannula may include a dedicated fixing means to be sutured to the skin.

A further aspect of the disclosure relates to a method of draining blood from a heart in a living body. In some embodiments, the method may involve the aforementioned method of placing a cardiac drainage cannula into the left atrium and, optionally, into the left ventricle. In particular, the method of draining blood includes the steps of: (a) inserting a cannula percutaneously into an internal jugular vein of the body, (b) advancing the cannula through the internal jugular vein and into the right atrium of the heart, (c) advancing the cannula through the atrial septum into the left atrium of the heart, placing a distal end portion of the cannula at least partially within the left atrium, a proximal end portion of the cannula may remain located external to the body, (d) receiving blood with the distal end portion of the cannula being placed at least partially within the left atrium of the heart and conducting the blood through the cannula from the distal end portion of the cannula to the proximal end portion of the cannula. Typically, the proximal end portion of the cannula is placed outside the body in order to drain the blood percutaneously out of the body and conduct the blood to an extracorporeal blood pump, for instance. In alternative embodiments, the proximal end portion of the drainage cannula may by placed with the patients body and be connected, for instance, with an implantable blood pump.

In accordance with at least some embodiments, the blood is being drained through the atrial septum, through the right atrium, through the internal jugular vein and, optionally, percutaneously out of the body. The blood may be received through corresponding inlets of the cannula into one or more lumens of the cannula, as described in more detailed below. The distal end portion may be partially placed within the right atrium and partially within the left ventricle. Accordingly, blood may be drained from the left atrium or from the left ventricle or simultaneously from both the left atrium and the left ventricle.

For instance, in some embodiment, the step (d) may comprise draining blood from the left atrium through at least one inlet of the cannula being placed within the left atrium. In some embodiments, step (c) comprises advancing the cannula from the left atrium through the mitral valve into the left ventricle of the heart, placing the distal end portion of the cannula partially within the left atrium and placing a distal end of the distal end portion of the cannula (i.e. the distal tip of the cannula) within the left ventricle. In some embodiments, step (d) comprises draining blood from the left atrium through at least one inlet of the cannula being placed within the left atrium, or draining blood from the left ventricle through at least one further inlet of the cannula being placed within the left ventricle, or draining blood from the left atrium through at least one inlet of the cannula being placed within the left atrium and simultaneously draining blood from the left ventricle through at least one further inlet of the cannula being placed within the left ventricle.

As mentioned above, the proximal end portion of the cannula may be connected to an extracorporeal blood pump, i.e., to a blood pump located external to the body. Examples of extracorporeal blood pumps include pulsatile blood pumps and continuous blood pumps. Examples of external blood pumps include, for instance, continuous blood pumps offered by Maquet GmbH (Getinge Group) under the mark of Rotaflow®, by Thoratec Corp. under the mark of Centrimag®, by Livallova PLC under the marks TandemHeart® and Revolution®, by Medos (Xenios) under the mark of Deltastream®. An example of a pulsatile external blood pumps is offered, for instance, by Berlin Heart GmbH under the mark of EXCOR®.

In some embodiments, the method may further comprise utilizing at least one extracorporeal or intracorporeal pressure sensor to measure at least one intracardiac blood pressure. This allows, for instance, for hemodynamical-guided left ventricular unloading and hemodynamical-guided left ventricular physiological mechanical circulatory support. The at least one intracorporeal pressure sensor may be permanently or removably fixed to the cannula. In this manner, additional (endoscopic or even surgical) procedures of placing intracorporeal sensors within the patient's body may be avoided.

The at least one measured intracardiac blood pressure may include one or more of: a first pressure $P_1$ indicative of blood pressure within the right atrium, a second pressure $P_2$ indicative of blood pressure within the left atrium, and/or a third pressure $P_3$ indicative of blood pressure within the left ventricle. In the following, pressure $P_1$ will also be referred to as right atrial pressure, pressure $P_2$ will also be referred to as left atrial pressure, and pressure $P_3$ will also be referred to as left ventricular pressure.

In some embodiments, the at least one pressure sensor may comprise, for instance, at least one intracorporal pressure sensor selected from: at least one first pressure sensor permanently or removably fixed to the cannula and located within the right atrium, at least one second pressure sensor permanently or removably fixed to the distal end portion of the cannula and located within the left atrium, at least one third pressure sensor permanently or removably fixed to the distal end portion of the cannula and located within the left ventricle. For instance, the first pressure sensor may be located within the right atrium and used to measure the first pressure $P_1$ indicative of blood pressure within the right atrium, the second pressure sensor may be located within the left atrium and used to measure the second pressure $P_2$ indicative of blood pressure within the left atrium, and/or the third pressure sensor may be located within the left ventricle and used to measure the third pressure $P_3$ indicative of blood pressure within the left ventricle. The measurements of the first, second and/or third pressures may be performed continuously and concurrently.

In the following the first pressure sensor will also be referred to as right atrial pressure sensor, the second pressure sensor will also be referred to as left atrial pressure sensor and the third pressure sensor will also be referred to as left ventricular pressure sensor. It should be noted, however that in some embodiments, only one or two of the pressure sensors may be realized/used. For instance, only the second (left atrial) pressure sensor and the third (left ventricular) pressure sensor may be used and/or present.

Additionally, or alternatively, the at least one pressure sensor may comprise, for instance, at least one external pressure sensor located external to the body.

In some embodiments, as described in more detail below, the cannula may include at least one pressure line (pressure lumen). The at least one pressure line may include at least one inlet located at or proximally to the distal end portion of the cannula, at least one outlet located at the proximal end portion of the cannula and connectable to one or more external pressure sensors, and at least one lumen fluidly connecting the at least one inlet with the at least one outlet of the at least one pressure line. In some embodiments, at least one of the at least on inlet is located, for instance, at a location selected from a location within the right atrium, a location within the left atrium and/or a location within the left ventricle.

The at least one external pressure sensor may be used, for instance, to measure a pressure of blood being percutaneously drained from the right atrium, from the left atrium and/or from the left ventricle through the at least one pressure line of the cannula. For instance, the at least one external pressure sensor may include one, two or three external pressure sensors. For instance, a first external pressure sensor may connected to a first (right atrial) pressure line and used to measure the first (right atrial) pressure $P_1$ indicative of blood pressure within the right atrium, the second external pressure sensor may connected to a second (left atrial) pressure line and used to measure the second pressure $P_2$ indicative of blood pressure within the left atrium, and/or a third external pressure sensor may connected to the third (left ventricular) pressure line and used to measure the third pressure $P_3$ indicative of blood pressure within the left ventricle. As in case of the aforementioned intracorporeal pressure sensors placed at locations within the heart, the measurements of the pressures $P_1$, $P_2$, and/or $P_3$ may be performed continuously and concurrently.

Some embodiments may comprise, for instance, controlling the external blood pump by means of a controller utilizing one or more of the at least one measured intracardiac blood pressures. For instance, one or more of the aforementioned blood pressures $P_1$, $P_2$, and $P_3$ measured by means of the aforementioned intracorporeal or extracorporeal pressure sensors may be used for automatically controlling the blood pump, thereby allowing a hemodynamical-guided control of the blood pump and/or the onset of a right-sided or left-sided heart failure, as described in more detail below.

For instance, the controller may be configured to automatically adjusts in (synchronous) real-time one or more adjustable pump parameters of the blood pump, such as, for instance, the pump speed, in response to signals received from the at least one intracorporeal or extracorporeal pressure sensor. The received signals may be indicative, for instance, of one or more of blood pressures $P_1$, $P_2$, and $P_3$. The controller may also be configured to automatically trend the measured blood pressures and/or automatically compared the measured blood pressures with one or more thresholds.

In some embodiments, one or more of the at least one measured blood pressures may be utilized to determine or detect at least one of: a degree or an amount of right ventricular unloading, a precursor or an onset of right ventricular failure, a degree or an amount of left ventricular unloading, and/or a precursor or an onset of left ventricular failure. Accordingly, the step of controlling the external blood pump may depend on one or more of the determined degree or amount of right ventricular unloading, the determination or detection of a precursor or onset of right ventricular failure, the determined degree or amount of left ventricular unloading, and/or the determination or detection of an precursor or onset of left ventricular failure. This can be done, for instance, using, for instance, of one or more of the intracardiac blood pressures $P_1$, $P_2$, and $P_3$, as described in greater detail below. For instance, when draining blood only from the left atrium, the pressures $P_1$ and $P_2$ may be used. When draining blood from both the left atrium and from the left ventricle, only $P_1$ and $P_2$, or only N and $P_3$, only $P_2$ and $P_3$, or all three pressures $P_1$, $P_2$, and $P_3$ may be used for instance.

Hence, by means of the hemodynamical guided physiological control of the degree of the unloading, overstretching of the left or right ventricle can be avoided (i.e. too large ventricular preload) as well as a too extensive unloading of the left atrium and left ventricle which may result in emptying of the right atrium or left ventricle, or suction, or increase the risk of right ventricular failure.

For instance, measured blood pressure $P_1$, i.e., the blood pressure measured within the right atrium may be used as an approximation or surrogate of the central venous pressure (CVP), i.e., $P_1$=CVP. As explained in more detail below, fulfillment of the condition $P_1$=CVP>10 mmHg may be used, for instance, as a precursor or as an indicator of heart failure, or more particularly as a precursor or as an indicator of right ventricular failure.

Additionally, or alternatively, measured pressure $P_2$, i.e., the blood pressure within the left atrium, may be used as an approximation or surrogate of the pulmonary capillary wedge pressure (PCWP), i.e., $P_2$=PCWP. As explained in more detail below, fulfillment of the condition $P_2$=PCWP>15 mmHg (or, alternatively, $P_2$=PCWP>20 mmHg) may be used, for instance, as a precursor or as an indicator of heart failure, or more particularly as a precursor or as an indicator of right ventricular failure. Furthermore, since measured blood pressures as $P_1$ and $P_2$ are usually close to each other, i.e. $P_1 \approx P_2$, pressure $P_1$ may be used as an approximation or surrogate of $P_2$, or vice versa.

Additionally, or alternatively, measured blood pressure $P_3$ within the left ventricle may be used an approximation or surrogate of the left ventricular end-diastolic pressure (LVEDP), i.e., $P_3$=LVEDP. As explained in more detail below, fulfillment of the condition $P_3$=LVEDP>15 mmHg may be used, for instance, as a precursor or as an indicator of heart failure, or more particularly as a precursor or as an indicator of left ventricular failure.

In some embodiments, the measured blood pressures, e.g., $P_1$, $P_2$, and/or $P_3$ are continuously and synchronously monitored, for instance, automatically using a blood pump controller and/or a blood pressure monitoring device. In particular, the blood pump controller and/or blood pressure monitoring device may be configured to determine whether one or more of the following conditions is fulfilled: $P_1$=CVP>10 mmHg, $P_2$=PCWP>15 mmHg and/or $P_3$=LVEDP>15 mmHg, and, optionally, to generate a corresponding alert signal if one or more of these conditions are determined to be fulfilled. Of course, different threshold values for pressures $P_1$, $P_2$, and $P_3$ could be used as well, the above values only being provided as possible examples.

In some embodiments, the blood may be percutaneously drained from the heart at a flow rate corresponding to 60% to 80% of a cardiac output of the heart. As explained in more detail below, the cardiac output (CO) may be determined using the relation cardiac output (CO)=heart rate (HR)× stroke volume (SV). Cardiac output (CO) may be measured, for instance, in ml/minute, heart rate (HR) in beats/minute, stroke volume (SV) in ml/beat. The current stroke volume (SV) of the heart depends on the preload, afterload, and contractility of the heart. Hence, for determining stroke volume, the relation SV=EDV-ESV may be used, wherein EDV is the end-diastolic volume and ESV is the end-systolic volume. The current end-diastolic and end-systolic volumes may be determined from current blood pressure values, for instance, by using a nonobligatory volume-pressure loop.

In some embodiments, the percutaneously drained blood is returned into the body, for instance, by percutaneously infusing the blood into a vein and/or into an artery of the body, for example, via an arterial perfusion cannula. Examples of suitable arteries include, among others, the right or left femoral artery and the right or left subclavian artery. By returning the drained blood back into the body, the mechanical circulatory support loop is closed. Optionally, the percutaneously drained blood may be oxygenated outside the body, for instance, the drained blood may be passed through an extracorporeal membrane oxygenation (ECMO) device. The cardiac support may be performed for several days or even weeks in order to unload the left atrium and the left ventricle and to promote the recovery of the left atrium and ventricle. In sum, the components used form a mechanical circulatory support system or left ventricular assist device.

A further aspect of the disclosure relates to a cardiac drainage cannula for draining blood from a heart. The cardiac drainage cannula may be used, for instance, for carrying out any of the methods described herein. Accordingly, any feature of drainage cannulas that have been described above in the context of the proposed methods may also be implemented with the proposed drainage cannula.

The cardiac drainage cannula comprises an elongate body including a proximal end portion, a distal end portion, and one or more lumens which extend through the elongate body from the distal end portion to, for instance, the proximal end portion or the distal tip of the elongate body. In some embodiments, the cannula may comprise at least one inlet at the distal end portion or at the distal tip of the elongate body and at least one proximal outlet at the proximal end portion of the elongate body, the at least one inlet being in fluid communication with the at least one outlet via the at least one lumen. The cannula may further include, at its proximal end, coupling means configured to fluidly coupling the cannula (i.e. one or more of its lumens) to one or more devices, e.g. to an extracorporeal blood pump and/or to extracorporeal pressure sensors.

In some embodiments, the at least one inlet may include, for instance, a left ventricular drainage inlet located at a distal tip of the elongate body and a left atrial drainage inlet located proximal to the left ventricular drainage inlet. In some embodiments, the at least one lumen of the elongate body includes a main drainage lumen or only one single drainage lumen. The left ventricular drainage inlet and the left atrial drainage may be in fluid communication with the main drainage lumen or the single drainage lumen of the elongate body. Alternatively, the cannula may include no left ventricular draining inlet but only one or more left atrial draining inlets at its distal tip.

As described above, the cardiac drainage cannula may further comprise at least one pressure sensor. In some embodiments, the at least one pressure sensor comprises at least one of: a right atrial pressure sensor permanently or removably fixed to the elongate body and configured to measure blood pressure within the right atrium of a heart, a left atrial pressure sensor permanently or removably fixed to the distal end portion of the elongate body and configured to measure blood pressure within the left atrium of a heart, and/or a left ventricular pressure sensor permanently or removably fixed to the distal end portion of the elongate body and configured to measure blood pressure within the left ventricle of a heart.

The at least one pressure sensor may include for instance, a common pressure transducer, a Micro-Electro-Mechanical-System (MEMS) sensor, or a fiber optic pressure sensor. One or more of the aforementioned right atrial pressure sensor, a left atrial pressure sensor and left ventricular pressure sensor may be, for instance, a MEMS sensor or fiber optic pressure sensor. The MEMS sensor or fiber optic pressure sensor may, for instance, be integrated or embedded into the elongated body, in particular, integrated or embedded into a wall of the elongate body.

In some embodiments, the at least one lumen of the elongate body includes at least one of: a right atrial pressure line extending from a proximal outlet of the right atrial pressure line at the proximal end portion of the elongate body to a right atrial inlet of the right atrial pressure line located at the distal end portion of the elongate body, a left atrial pressure line extending from a proximal outlet of the left atrial pressure line at the proximal end portion of the elongate body to a left atrial inlet of the left atrial pressure line located at the distal end portion of the elongate body, and/or a left ventricular pressure line extending from a proximal outlet of the left ventricular pressure line at the proximal end portion of the elongate body to a left ventricular inlet of the left atrial pressure line located at the distal tip of the elongate body. Each of the proximal outlets may be connectable to a dedicated pressure transducer, as described herein.

In some embodiments, the cannula may comprise a securing means for securing the proximal end portion of the elongated body of the cannula to a skin portion adjacent to a percutaneous insertion site of the cannula. In some embodiments, the securing means may include a fixation member having a lumen, such as an O-ring, and be configured to slidably receive therethrough the proximal end portion of elongate body of the cannula. The fixation member may include, for instance, at least one hole for receiving a suture thread therethrough for suturing the securing means to a skin portion, as described herein.

The cardiac drainage cannula may be designed to have adequate dimensions to fit the specific conditions and needs of an individual patient. The cannula may, for instance, be manufactured in accordance with one of a plurality of size classes of the cannula. Table 1 below provides several examples of possible size classes, e.g. size classes I to VII. Each size class may be characterized by values, or ranges of values, for one or more of the following dimencions, for example:

B: body diameter or outer diameter of elongate body,
C: insertable length or length of elongate body from distal end to proximal end D: proximal insertable length or distance of proximal end of elongate body and one of LA pressure sensor, inlet of LA pressure line, and/or LA drainage inlet,
E: axial distance between RA pressure sensor and/or inlet of RA pressure line and one of LA pressure sensor, inlet of LA pressure line and LA drainage inlet,
F: axial distance between one of LA pressure sensor, inlet of LA pressure line and/or LA drainage inlet and one of LV pressure sensor, inlet of LV pressure line and/or LV drainage inlet,
G: axial distance between one of RA sensor and/or inlet of RA pressure line and one of LV pressure sensor, inlet of LV pressure line and/or LV drainage inlet.

Exemplary values, or ranges of values, are provided for each of the dimensions B to F, and for each of exemplary size classes I to VIII, in Table 1. It is noted that the examples for any of the exemplary definitions of dimensions B to G as provided in the second line of Table 1 may be replaced by any of the examples for B to G as provided in the in the list above. Also, the patient weight ranges in the second column from the left for defining the size classes I to VII, as well as the connector sizes, are provided as possible examples only.

the left atrial pressure sensor in range of 1 cm to 5 cm. In some embodiments, the right atrial pressure inlet may be, for instance, located proximal to the distal tip of the elongate member. In some embodiments, a distance between the right atrial pressure inlet and the distal tip may be, for instance, in range of 3 cm to 13 cm. In some embodiments, the left atrial pressure inlet may be, for instance, located proximal to the distal tip of the elongate member. In some embodiments, a distance between the left atrial pressure inlet and the distal tip may be, for instance, in range of 2 cm to 8 cm. In some embodiments, the right atrial pressure inlet may be, for instance, located proximal to the left atrial pressure inlet. In some embodiments, a distance between the right atrial pressure inlet and the left atrial pressure inlet in range of 1 cm to 5 cm.

A further aspect of the disclosure relates to a mechanical circulatory support system. The system may be configured for providing mechanical circulatory support in accordance with the methods described herein. The system may include, for instance, the cardiac drainage cannula for draining blood from a heart as described herein. Accordingly, any features, system components, and method steps that are described

TABLE 1

| Size Class | weight | Connector Size | B e.g., Body Diameter size | | C e.g. Insertable length | D e.g., Proximal Insertable length to LA drainage | E e.g., P1 to LA drainage length | F e.g., LA drainage to LV drainage tip length | G e.g. P1 to LV drainage tip length |
|---|---|---|---|---|---|---|---|---|---|
| | | | Fr. | mm | cm | cm | cm | cm | cm |
| I | 4-9 kg | 13 Fr. | ¼ in | 13 | 4.3 | 16-22 | 7-13 | 1-2 | 2-3 | 3-5 |
| II | 10-16 kg | 17 Fr. | ¼ in | 17 | 5.6 | 26-32 | 17-23 | 2-3 | 4-5 | 6-8 |
| III | 17-25 kg | 19 Fr. | ¼ in | 19 | 6.3 | 36-42 | 27-33 | 3-4 | 5-6 | 8-10 |
| IV | 26-40 kg | 21 Fr. | ⅜ in | 21 | 7 | 46-52 | 37-43 | 4-5 | 7-8 | 11-13 |
| V | 41-50 kg | 23 Fr. | ⅜ in | 23 | 7.6 | 46-52 | 37-43 | 4-5 | 7-8 | 11-13 |
| VI | 51-70 kg | 27 Fr. | ⅜ in | 27 | 9 | 46-52 | 37-43 | 4-5 | 7-8 | 11-13 |
| VII | >70 kg | 31 Fr. | ⅜ in | 31 | 10.3 | 46-52 | 37-43 | 4-5 | 7-8 | 11-13 |

Accordingly, in some embodiments, an outer diameter of the elongate body may be for instance, in a range of 4 mm to 11 mm. A length of the elongate body may be, for instance, in a range of 16 cm to 52 cm. In some embodiments, a distance between the left ventricular drainage inlet and the left atrial drainage inlet may be, for instance, in a range of 2 cm to 8 cm. In some embodiments, the right atrial pressure sensor may be, for instance, located proximal to the distal tip of the elongate member. In some embodiments, a distance between the right atrial pressure sensor and the distal tip may be, for instance, in range of 3 cm to 13 cm. In some embodiments, the left atrial pressure sensor may be, for instance, located proximal to the distal tip of the elongate member. In some embodiments, a distance between the left atrial pressure sensor and the distal tip may be, for instance, in range of 2 cm to 8 cm. In some embodiments, the left ventricular pressure sensor may be, for instance, located at the distal tip of the elongate body. In some embodiments, the right atrial pressure sensor may be, for instance, located proximal to the left atrial pressure sensor. In some embodiments, a distance between the right atrial pressure sensor and herein in the context of the proposed drainage cannula or proposed methods may also be part of or implemented with the proposed circulatory support system. In particular, the system may include one or more of: an extracorporeal or implantable blood pump connectable to a drainage cannula and/or to a perfusion cannula, at least one pressure sensor as described herein, e.g. one or more external pressure sensors and/or one or more pressure sensors integrated into the drainage cannula, and a pump controller that may be integrated into the (extracorporeal or implantable) blood pump or a separate (extracorporeal or implantable) device connectable to the blood pump. The at least one pressure sensor may be arranged and configured to measure, for instance, one or more of the aforementioned blood pressures $P_1$, $P_2$, and/or $P_3$ and produce corresponding (e.g. electrical or optical) signals being indicative of or including information about the measured blood pressures. The pump controller may be configured to receive signals from the at least one pressure sensor, to determine measured blood pressure values on the basis of the signals, and/or to control the blood pump on the basis of the received signals of the pressure sensors.

The pump controller may be configured to automatically trend the measured blood pressures and/or compare the measured blood pressure with corresponding threshold values, for instance, as has described herein. For instance, the pump controller may be configured to adjust one or more pump parameters of the blood pump, such as pump speed or pump rate, on the basis of the measured blood pressures.

DETAILED DESCRIPTION

Figure 1:
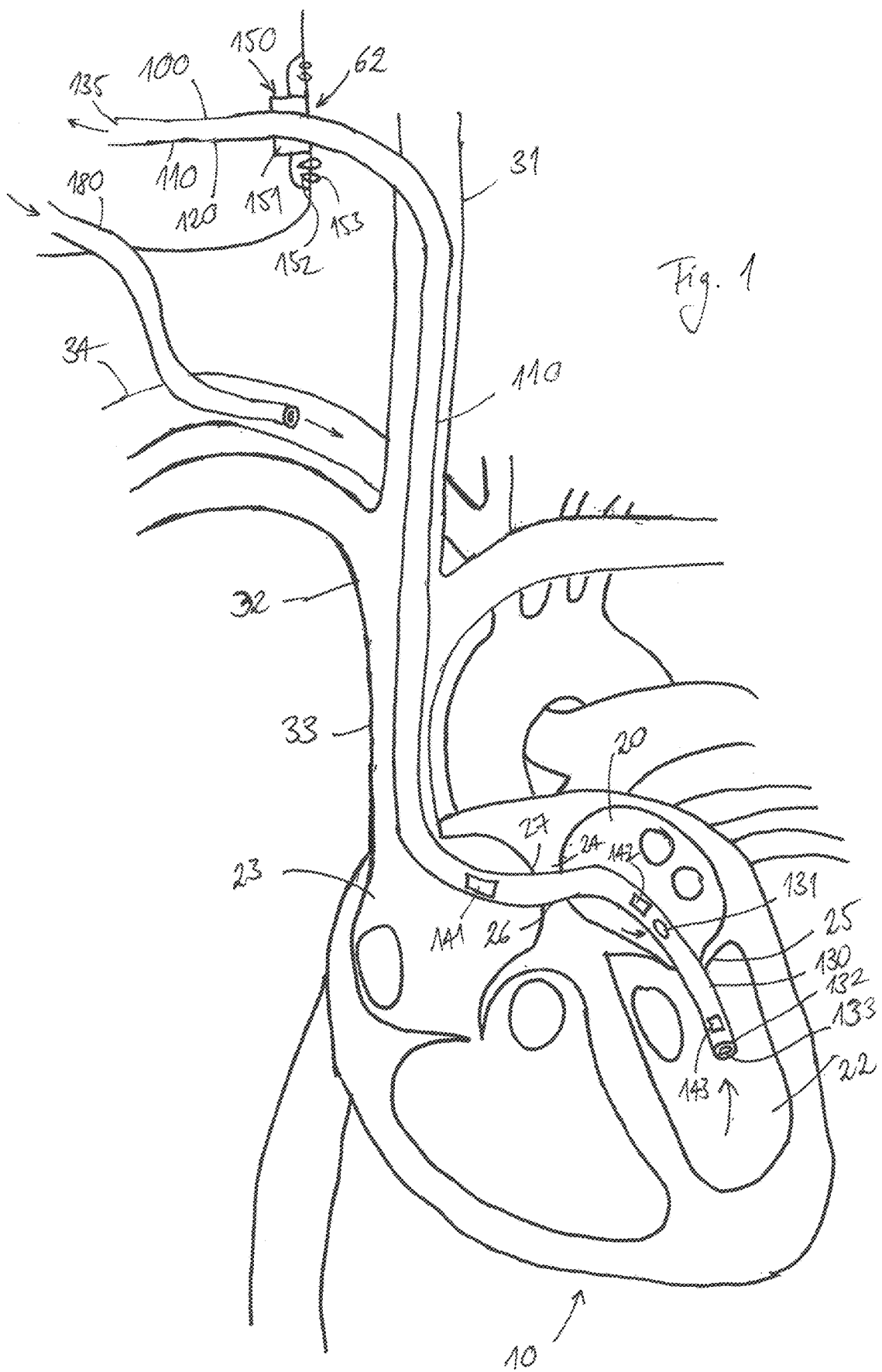
FIG. 1 schematically illustrates a cardiac drainage cannula, placed within a human heart and draining blood from the left atrium and the left ventricle of the heart, in accordance with example embodiments of the invention.

FIG. 1 schematically illustrates an exemplary embodiment of a cardiac drainage cannula 100 in accordance with the invention. The cannula 100 has been placed within a human heart 10 and is used to drain blood simultaneously from the left atrium 20 and the left ventricle 22 of the heart 10, in accordance with embodiments of the invention.

A. PLACEMENT OF CARDIAC DRAINAGE CANNULA

In the example illustrated in FIG. 1, the cannula 100 has been placed within the left atrium 20 and the left ventricle 22 of the heart 10 by (a) inserting the cannula 100 percutaneously into an internal jugular vein 31 of the body, (b) advancing the cannula 100 through the internal jugular vein 31 and into the right atrium 23 of the heart, and (c) advancing the cannula 100 through the atrial septum into the left atrium 20 of the heart 1 and through the mitral valve 25 further into the left ventricle 22 of the heart.

In the present exemplary embodiment, step (a) includes advancing the cannula 100 through a percutaneous puncture 62 which extends from an outer skin surface on the patient's neck through the skin 60, through tissue between skin and internal jugular vein 31, and through a wall of the internal jugular vein 31.

The percutaneous puncture 62 has been formed, for instance, by means of a needle (e.g. a trocar) without incising tissue and without using a scalpel or similar cutting tool. After puncturing the skin, the needle is advanced through the skin and towards the internal jugular vein 31, puncturing the wall of the internal jugular vein 31. The Seldinger technique is employed in the following manner. The needle used for forming the percutaneous puncture has a lumen. A guidewire is inserted through the lumen of the needle into the lumen of the internal jugular vein 31. The needle is subsequently removed, keeping the guidewire in place. The guidewire which may optionally include a pigtail, for instance, is then advanced along the path described above into the left atrium 23.

In the exemplary embodiment, the method further comprises an atrial septostomy which includes puncturing the atrial septum 24 with a sharp instrument to form a transseptal puncture 26 at the fossa ovalis 27. The sharp instrument may be, for instance, a transseptal needle, such as a Brockenbrough needle. The atrial septostomy may include passing a sheath (e.g. a Mullins sheath) over the guidewire into the right atrium 23. The sharp instrument may then be inserted and advanced through the sheath to the atrial septum 24 to form the transseptal puncture 26. The guidewire may subsequently be advanced through the transseptal puncture 26 and further through the mitral valve 25 into the left ventricle 22.

A dilatator, e.g. Mullin Mandrin, may be advanced over the guidewire though the transseptal puncture 26 to enlarge the transseptal puncture 26. After removing the instruments used for the atrial septostomy (particularly the sharp instrument, the sheath and the dilatator), the cannula 100 is inserted percutaneously and advanced over the guidewire along the path described above into the right atrium 23, through the transseptal puncture 26 into the left atrium 20, and through the mitral valve 25 into the left ventricle 22.

Before inserting the cannula 100, a dilatator may be inserted into the percutaneous puncture 62 in order to enlarge the puncture. Optionally, a scalpel may be used to further enlarge the puncture in order to facilitate advancing the dilatator.

After having placed the cannula 100, the guidewire may be removed. The cannula 100 may include a securing means (fixing means) 150 coupled to a proximal end portion 120 of an elongate body 110 of the cannula 100. The securing means 150 may include a fixation member 151 having a lumen, such as an O-ring, to slidably receive the proximal end portion 120 of the cannula 100. The fixation member 151 may further include, for instance, at least one hole 152 for receiving a suture thread 153 therethrough for suturing the securing means to a skin portion, as described herein. The fixation member 151 may optionally include a clamping mechanism to reduce the diameter of the lumen, thereby fixing the fixation member to the proximal end portion 120 of the cannula 100.

B. UNLOADING THE LEFT VENTRICLE AND PROVIDING MECHANICAL CIRCULATORY SUPPORT

After having placed the cardiac drainage cannula 100 within the heart 100, for example as described above, blood may be drained through the cannula 100 and may be provided, for example, to an extracorporeal pump (not shown). The proximal end portion 120 of the cannula 100 may extend outside the patient's body and connect to an extracorporeal blood pump which, for instance, may be one of the examples provided above, e.g., a pulsatile blood pump as offered by Berlin Heart GmbH under the mark of EXCOR®.

In the illustrated example, blood is being simultaneously drained from the left atrium 20 through a left atrial drainage inlet 131 at a distal end portion 130 of the elongate body 110 of the cannula 100 and from the left ventricle 22 through a left ventricular drainage inlet 133 at a distal tip 132 of the elongate body 110 of the cannula 100. In alternative examples, the cannula 100 ends within the left atrium 20 and blood is drained only from the left atrium 20.

In the present example, after optionally being loaded with pressure by means of the extracorporeal blood pump, and optionally after being passed through an extracorporeal membrane oxygenation (ECMO) device (not shown), the drained blood is infused back into the body, for example, via an arterial perfusion cannula 180 into the right subclavian artery or axillary artery. The cardiac support may be performed for several days or even weeks in order to unload the left atrium and the left ventricle and to promote the recovery of left heart. In this manner, a mechanical circulatory support system or left ventricular assist device is formed.

Further embodiments of cardiac drainage cannulas and mechanical circulatory support systems are illustrated in FIGS. 2 to 7 and described further below.

C. MEASURING INTRACARDIAC PRESSURE

In some embodiments, such as in the exemplary embodiments discussed with reference to FIGS. 1 to 7, the method of draining blood from the left atrium 20 and, optionally also from the left ventricle 22, may also include measuring and monitoring intracardiac pressures. The measure pressures may include, for instance, a first pressure $P_1$ indicative of blood pressure within the right atrium 23, a second pressure $P_2$ indicative of blood pressure within the left atrium 20, and/or a third pressure $P_3$ indicative of blood pressure within the left ventricle 22.

In the particular embodiment shown in FIG. 1, the cannula 110 includes a right atrial pressure sensor 141 located within the right atrium 23 for measuring $P_1$, a second left atrial pressure sensor 142 fixed to the distal end portion 130 of the cannula and located within the left atrium 20 for measuring $P_2$, and third left ventricular pressure sensor 143 fixed to the distal end portion 130 of the cannula 100 and located within the left ventricle 22 for measuring $P_3$. In alternative embodiments, only one or two of the three pressure sensors 141, 142, 143 may be present, for instance, only pressure sensors 141 and 142 for measuring only $P_1$ and $P_2$, or only pressure sensors 141 and 143 for measuring only $P_1$ and $P_3$, or only pressure sensors 142 and 143 for measuring only $P_2$ and $P_3$.

Some embodiments may comprise, for instance, controlling the external blood pump by means of a controller utilizing one or more of the at least one measured blood pressure. For instance, one or more of the aforementioned blood pressures $P_1$, $P_2$, and $P_3$ may be used for automatically controlling the blood pump. For instance, the controller may be configured to automatically adjusts in (synchronous) real-time one or more adjustable pump parameters of the blood pump, such as, for instance, the pump speed, in response to signals received from the at least one pressure sensor. The measurements of the first, second and/or third pressures $P_1$, $P_2$ and/or $P_3$ may be performed continuously and concurrently. Furthermore, the measured first, second and/or third pressures $P_1$, $P_2$ and/or $P_3$ may be trended and/or compared with respective thresholds, as explained in more detail below.

D. USING INTRACARDIAC PRESSURES FOR CONTROLLING MCS

In the following, a brief overview is provided of different intracardiac pressures and correlations between them and how these pressures and correlations may be utilized to assess, for instance, left-sided and/or right-sided heart failure in patients with mechanical circulatory support (MCS) and to provide, for instance, hemodynamical-guided left ventricular unloading.

Heart failure (HF) or congestive HF is caused by any condition that impairs cardiac function. In particular, left-sided heart failure is relatively common in patients with congestive HF and may subsequently cause right-sided heart failure. One of the most important hemodynamic indicators, particularly in the early postoperative period (after institution of MCS), is cardiac output. However, using one single cardiac parameter is often not sufficient to determine the appropriate therapeutic intervention. Therefore, an evaluation of different parameters in combination should be considered.

The goal of MCS is to maintain adequate systemic perfusion to preserve cerebral, myocardial and visceral function. Cardiac output (CO) is defined as the amount of blood ejected from the heart per minute, hence $$CO = SV \cdot HR \tag{Eq. 1}$$

where CO is cardiac output; SV is stroke volume and HR is heart rate. The normal range of cardiac output is about 4-8 l/min, but may vary depending on the body's metabolic needs. A more accurate determination of CO in a patient of any size is to take the body surface area (BSA) into account. Thus, a cardiac index (CI) can be calculated. For instance, du Bois equation may used to determine BSA, $$BSA = \sqrt{\frac{Ht \cdot Wt}{3600}} \tag{Eq. 2}$$

where Ht is the height of the patient in cm, Wt weight of the patient in kg, and BSA in m². The cardiac index (CI) can be calculated using $$CI = \frac{CO}{BSA} \tag{Eq. 3}$$

Using equations 2 and 3, the cardiac output (CO) may be determined based on CI and BSA as $$CO = CI \cdot BSA \tag{Eq. 4}$$

The normal range of CI is typically 2.5-4.0 l/min/m². Values of CI below 2.5 l/min/m² may be classified as HF, as an example.

Figure 1A:
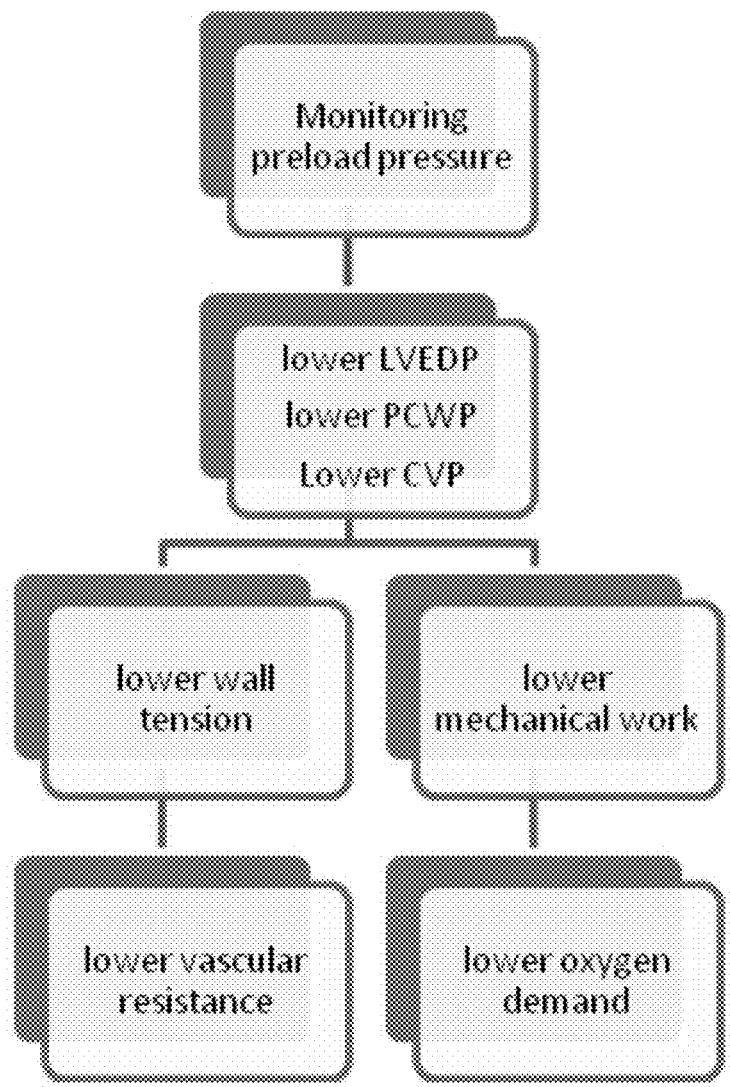
FIG. 1A illustrates an example Mechanical Circulatory Support (MCS) intervention, FIG. 2 schematically illustrates a cardiac drainage cannula in accordance with embodiments of the invention, FIG. 2A schematically illustrates a cross-section of the cardiac drainage cannula shown in FIG. 2, FIG. 3 schematically illustrates a mechanical circulatory support system in accordance with embodiments of the invention, FIG. 4 schematically illustrates a cardiac drainage cannula in accordance with embodiments of the invention, FIGS. 4A and 4B schematically illustrate a cross-section of the cardiac drainage cannula shown in FIG. 4, FIG. 5 schematically illustrates a mechanical circulatory support system in accordance with an embodiment of the invention, FIG. 6 schematically illustrates a cardiac drainage cannula in accordance with a further embodiment of the invention, FIGS. 6A and 6B schematically illustrate a cross-section of the cardiac drainage cannula shown in FIG. 6, FIG. 7 schematically illustrates a mechanical circulatory support system in accordance with embodiments of the invention.

As in equation 1 above, stroke volume (SV) is governed by preload, afterload, and contractility. As illustrated in the simplified overview chart of an example MCS intervention shown in FIG. 1A, a crucial part of MCS is to obtain a relatively normal preload pressure, first to reduce wall stress in the ventricles and second to facilitate good drainage of the cannulas used in MCS and to generate sufficient systemic perfusion throughout the body.

As discussed in more detail below, high end-diastolic preload pressures often correlate with elevated values of one or more of the following blood pressures: left ventricular end-diastolic pressure (LVEDP), pulmonary capillary wedge pressure (PCWP); and central venous pressure (CVP). Therefore, when delivering MCS, increased levels of LVEDP, PCWP, and CVP should be lowered, if possible, in order to maintain a relatively normal preload pressure.

Preload can be defined as the initial stretching of myocardial muscle fibers (cardiac myocytes) prior to contraction. The Frank-Starling mechanism explains this relation between myocardial fiber length and force of contraction (stroke) in response to changes in venous return (volume). In a patient with cardiogenic shock caused by acute myocardial infarction or patients with chronic heart failure the Frank-Starling curve typically shifts downward such that a given pressure results in a lower stroke volume, despite relatively constant parameters in all other conditions (afterload, etc.). Therefore, continuous monitoring of preload pressure can be a valuable tool in MCS, thus allowing clinicians to adjust MCS therapy accordingly.

As already mentioned above, central venous pressure (CVP), pulmonary capillary wedge pressure (PCWP), and left ventricular end-diastolic pressure (LVEDP) are particularly useful for assessing left-sided and/or right-sided heart failure.

In particular, central venous pressure may be used, for instance, to determine volume status and right ventricular function. Thus, CVP correlates with right ventricular end-diastolic pressure. The normal range of CVP is between 0 to 8 mmHg for neonate/infant, between 2 to 6 mmHg for pediatric/adult. Currently, CVP is measured using a central venous catheter.

Pulmonary capillary wedge pressure (PCWP) may be used, for instance, to determine left ventricle function. PCWP correlates with left atrial pressure (LAP) and LVEDP. The normal range for PCWP is 2 to 12 mmHg. Currently, these pressures are measured using a Swan-Ganz catheter.

At the diastole of the right ventricle, particularly at the end of the diastole of the right ventricle, the following relationships of blood pressures typically hold:

RAP=RVEDP,RVEDP<PADP, and
PADP=LAP=LVEDP, wherein RAP stands for right atrial pressure, RVEDP for right ventricular end-diastolic pressure, PADP for pulmonary artery diastolic pressure, LAP for left atrial pressure, and LVEDP for left ventricular end-diastolic pressure.

Moreover, at the diastole of the left ventricle, particularly at the end of the diastole of the left ventricular ventricle, the following relationships of blood pressures typically hold:

PCWP≈LAP≈LVEDP, wherein PCWP stands for pulmonary capillary wedge pressure, LAP for right atrial pressure, and LVEDP for left ventricular end-diastolic pressure.

HF is often manifested in relatively high end-diastolic preload pressure. Typical ranges for the following preload pressures in patient with HF are, for instance, CVP>10 mmHg,PCWP>15 mmHg, and LVEDP>15 mmHg.

The aforementioned pressures $P_1$, $P_2$, and $P_3$, as measured using the proposed cardiac drainage cannula, may be used as surrogates or approximations of CVP, PCWP, and LVEDP, respectively. For instance, one may define $P_1$=CVP, $P_2$=PCWP, and $P_3$=LVEDP. Accordingly, one may define the following HF criteria based on $P_1$, $P_2$, and $P_3$:

$P_1$>10 mmHg,$P_2$>15 mmHg, and $P_3$>15 mmHg.

Accordingly, elevated values of $P_1$, e.g. $P_1$ being larger than a first threshold, for instance, $P_1$>10 mmHg, may be considered as an indicator of right ventricular failure. Moreover, elevated values of $P_2$, e.g. $P_2$ being larger than a second threshold, for instance, $P_2$>15 mmHg, may be considered as an indicator of left ventricular failure. Additionally, or alternatively, elevated values of $P_3$, e.g. $P_3$ being larger than a third threshold, for instance, $P_3$>15 mmHg, may be considered as an (additional or alternative) indicator of left ventricular failure.

In some embodiments, one or more of the at least one measured blood pressure may be utilized to determine or detect at least one of: a degree or an amount of right ventricular unloading, a precursor or an onset of right ventricular failure, a degree or an amount of left ventricular unloading, and/or a precursor or an onset of left ventricular failure. This can be done, for instance, using, for instance, of one or more of blood pressures $P_1$, $P_2$, and $P_3$, as described in more detail further below.

In some embodiments, the step of controlling the external blood pump may depend on one or more of the determined degree or amount of right ventricular unloading, the determination or detection of a precursor or onset of right ventricular failure, the determined degree or amount of left ventricular unloading, and/or the determination or detection of an precursor or onset of left ventricular failure.

For instance, measured blood pressure $P_1$, i.e., the blood pressure measured within the right atrium may be used as an approximation or surrogate of the central venous pressure (CVP), i.e., $P_1$=CVP. As explained in more detail below, fulfillment of the condition $P_1$=CVP>10 mmHg may be used, for instance, as a precursor or as an indicator of heart failure, or more particularly as a precursor or as an indicator of right ventricular failure.

Additionally, or alternatively, measured pressure $P_2$, i.e., the blood pressure within the left atrium, may be used as an approximation or surrogate of the pulmonary capillary wedge pressure (PCWP), i.e., $P_2$=PCWP. As explained in more detail below, fulfillment of the condition $P_2$=PCWP>15 mmHg (or, alternatively, $P_2$=PCWP>20 mmHg) may be used, for instance, as a precursor or as an indicator of heart failure, or more particularly as a precursor or as an indicator of right ventricular failure. Furthermore, since measured blood pressures as $P_1$ and $P_2$ are usually close to each other, i.e. $P_1$≈$P_2$, pressure $P_1$ may be used as an approximation or surrogate of $P_2$, or vice versa.

Additionally, or alternatively, measured blood pressure $P_3$ within the left ventricle may be used an approximation or surrogate of the left ventricular end-diastolic pressure (LVEDP), i.e., $P_3$=LVEDP. As explained in more detail below, fulfillment of the condition $P_3$=LVEDP>15 mmHg may be used, for instance, as a precursor or as an indicator of heart failure, or more particularly as a precursor or as an indicator of left ventricular failure.

In some embodiments, the measured blood pressures, e.g., $P_1$, $P_2$, and/or $P_3$ are continuously and synchronously monitored, for instance, automatically using a blood pump controller and/or a blood pressure monitoring device. In particular, the blood pump controller and/or blood pressure monitoring device may be configured to determine whether one or more of the following conditions is fulfilled: $P_1$=CVP>10 mmHg, $P_2$=PCWP>15 mmHg and/or $P_3$=LVEDP>15 mmHg, and, optionally, to generate a corresponding alert signal if one or more of these conditions are determined to be fulfilled. Of course, different threshold values for pressures $P_1$, $P_2$, and $P_3$ could be used as well, the above values only being provided as possible examples.

In some embodiments, the blood may be percutaneously drained from the heart at a flow rate corresponding to 60% to 80% of a cardiac output of the heart. The cardiac output (CO) may be determined using the relation cardiac output (CO)=heart rate (HR)×stroke volume (SV). Cardiac output (CO) may be measured, for instance, in ml/minute, heart rate (HR) in beats/minute, stroke volume (SV) in ml/beat. The current stroke volume (SV) of the heart depends on the preload, afterload, and contractility of the heart. Hence, for determining stroke volume, the relation SV=EDV−ESV may be used, wherein EDV is the end-diastolic volume and ESV is the end-systolic volume. The current end-diastolic and end-systolic volumes may be determined from current blood pressure values, for instance, by using a volume-pressure loop.

The above techniques allow for hemodynamical guided left ventricular unloading. The following additional examples implement these principles.

E. ADDITIONAL EXAMPLES

FIG. 2 shows a further embodiment of a cardiac drainage cannula 200. The cannula 200 includes an elongate body 210 including a proximal end portion 220, a distal end portion 230 and a main drainage lumen 234. The elongate body 210 further includes a left atrial drainage inlet 231 and a left ventricular drainage inlet 232 at the distal end portion 230 which are in fluid communication with the drainage lumen 234. A proximal drainage outlet 235 is located at the proximal end portion 220 of the cannula body 210.

Figure 4:
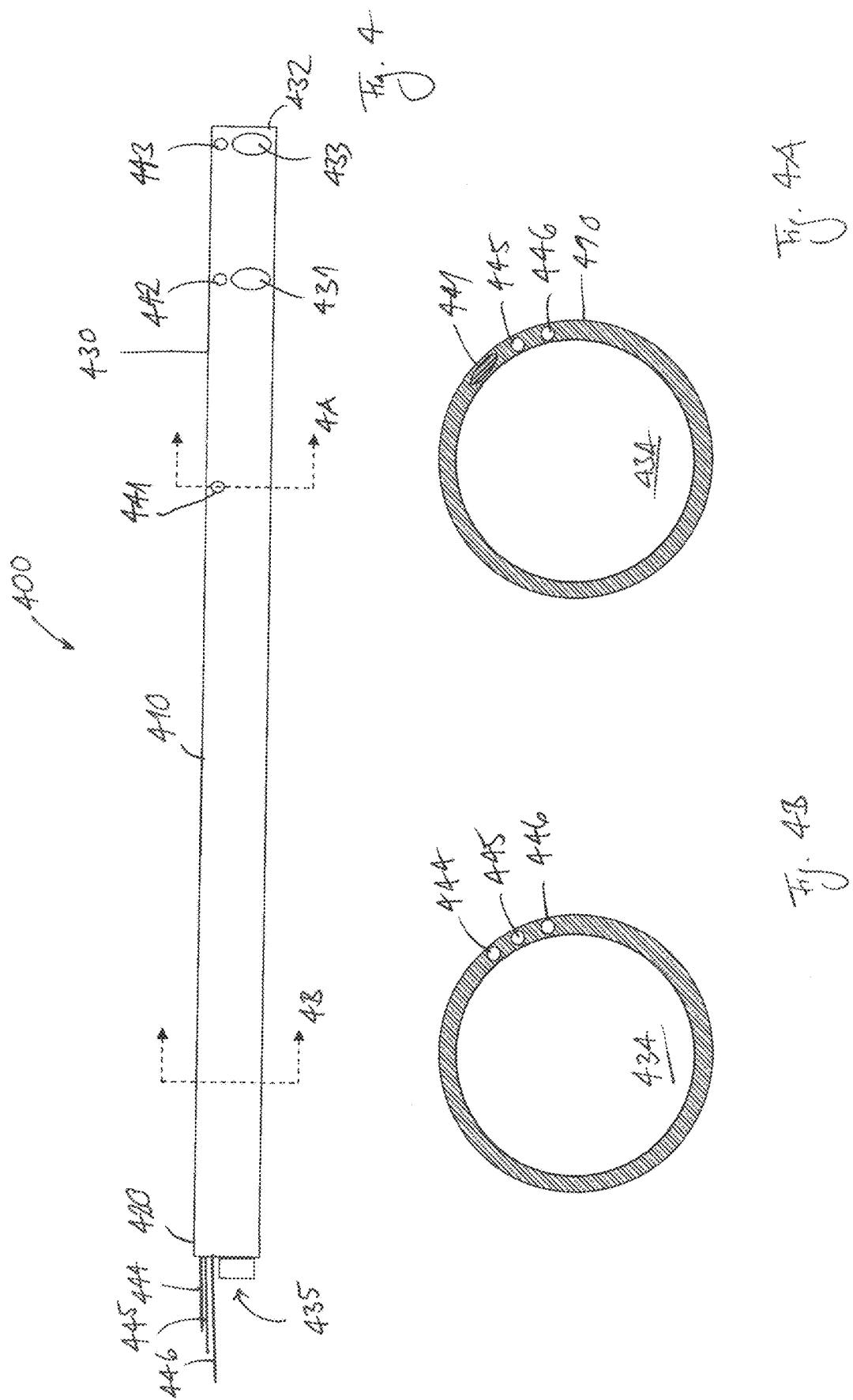

It is noted that the cannula shown in FIGS. 2, 4, 6 are depicted in a straight configuration. However, the cannula disclosed herein may have curved portions. In particular, the distal end portion may be pre-shaped or precurved, for instance, so as to match the anatomical dimensions and relative positions of structures of a typical or individual human heart when being placed within the heart as described herein.

The elongate body 210 further comprises a right atrial pressure lumen 247 extending from a proximal outlet of the right atrial pressure line at the proximal end portion of the elongate body 210 to a right atrial inlet 244 of the right atrial pressure lumen. A left atrial pressure lumen 248 extends from a proximal outlet of the left atrial pressure lumen 248 at the proximal end portion 220 of the elongate body 210 to a left atrial inlet 245 of the left atrial pressure lumen 248 located at the distal end portion 230 of the elongate body. A left ventricular pressure lumen extends from a proximal outlet of the left ventricular pressure lumen at the proximal end portion 220 of the elongate body 210 to a left ventricular inlet 246 of the left atrial pressure lumen 247 located at the distal tip 232 of the elongate body. Each of the proximal outlets of the pressure lumen 247, 248, and 249 are configured to be connected with a corresponding external pressure sensor, as described with reference to FIG. 3 further below.

The cannula 200 may be sized to have dimension B to G in accordance with one of the size classes as described above and as indicated in Table 1, for instance. For instance, the cannula may be sized in accordance to size class I or, alternatively, in accordance with any other of size classes II to VII.

FIG. 2A shows a cross-section of cannula 200 along the dashed line indicated in FIG. 2. It is noted that the cross-sectional shape of the pressure lumen 247, 248 and 249 is only exemplary and other cross-sectional shapes and arrangements of pressure lumen 247, 248 and 249 are possible as well.

Figure 3:
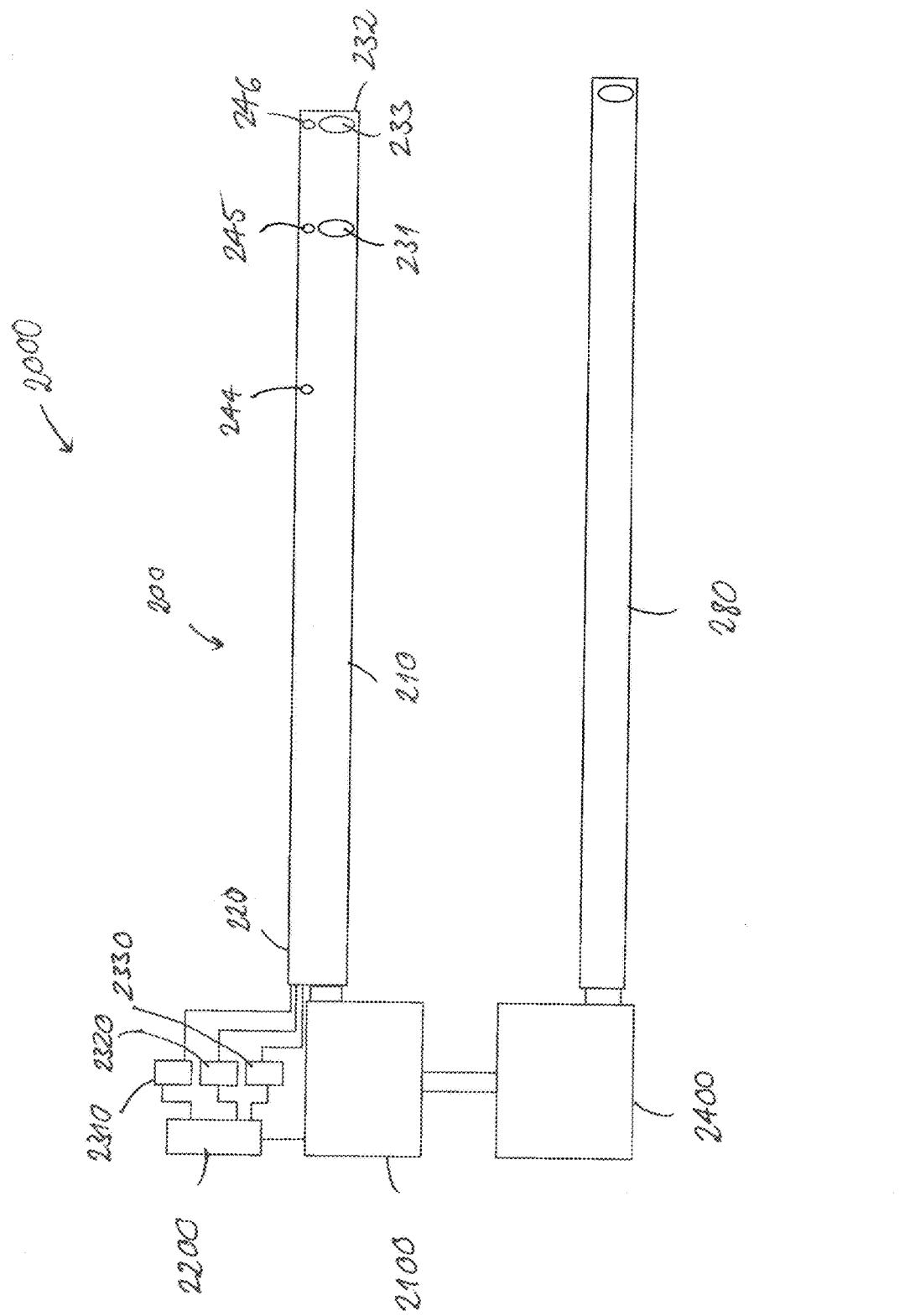

FIG. 3 shows an example of a mechanical circulatory support system 2000 in accordance with aspects of the present invention. The system 2000 is configured for providing mechanical circulatory support in accordance with the methods described herein and as described, for instance, with reference to FIG. 1 above. The system 2000 may include, for instance, the cardiac drainage cannula 200 shown in FIGS. 2 and 2A above for draining blood from a heart as described herein. The system may further include an extracorporeal blood pump 2100 connected to the drainage cannula 200 and, via an extracorporeal oxygenation device 2400 of the system 2000, to a perfusion cannula 280. The system further includes a pump controller 2200 connected to the blood pump 2100 and to external pressure sensors 2310, 2320, 2330. The pressure sensors 2310, 2320, 2330 are connected to the outlets of the pressure lumen 2347, 248, and 249 and configured to measure, the aforementioned blood pressures $P_1$, $P_2$, and $P_3$, respectively, and produce corresponding signals being indicative of or including information about the measured blood pressures. The pump controller 2100 is configured to receive the pressure signals from each of the pressure sensors 2310, 2320, 2330, to determine measured blood pressure values on the basis of the signals, and to control the blood pump 2100 on the basis of the received signals of the pressure sensors 2310, 2320, 2330. The measurements of the pressures $P_1$, $P_2$, and/or $P_3$ may be performed continuously and concurrently.

The pump controller 2100 may be configured to automatically trend the measured blood pressures and/or compare the measured blood pressure with corresponding threshold values, for instance, as has described herein. For instance, the pump controller 2200 may be configured to adjust one or more pump parameters of the blood pump 2100, such as pump speed or pump rate, on the basis of the measured blood pressures.

FIG. 4 shows a further embodiment of a cardiac drainage cannula 400 in accordance with the invention. The cannula 400 includes an elongate body 410 including a proximal end portion 420, a distal end portion 430 and a main drainage lumen 434. The elongate body 410 further includes a left atrial drainage inlet 431 and a left ventricular drainage inlet 432 at the distal end portion 430 which are in fluid communication with the drainage lumen 434. A proximal drainage outlet 435 of the drainage lumen 434 is located at the proximal end portion 420 of the cannula body 410.

In the cannula 400 further comprises a right atrial pressure sensor 441 integrated into a wall of the elongate body 410, as illustrated in the cross-sectional view shown in FIG. 4A along the corresponding dashed line in FIG. 4. During use, the left atrial pressure sensor 441 is located within the right atrium 23 for measuring pressure $P_1$, a second left atrial pressure sensor 442 is integrated into the wall of the distal end portion 430 of the cannula 400. During use, left atrial pressure sensor 442 is located within the left atrium 20 for measuring pressure $P_2$. A third left ventricular pressure sensor 443 is integrated into the wall of the distal end portion 430 of the cannula 400. During use, left ventricular pressure sensor 443 is located within the left ventricle 22 for measuring pressure $P_3$. In alternative embodiments, only one or two of the three pressure sensors 441, 442, 443 may be present, for instance, only pressure sensors 441 and 442 for measuring only $P_1$ and $P_2$, or only pressure sensors 441 and 443 for measuring only $P_1$ and $P_3$, or only pressure sensors 442 and 443 for measuring only $P_2$ and $P_3$. As in case of the pressure sensors 141, 142, 143 of the cannula shown in FIG. 1, the measurements of the pressures $P_1$, $P_2$, and/or $P_3$ may be performed continuously and concurrently.

The cannula 400 may be sized to have dimension B to G (dimensions omitted in FIG. 4) in accordance with one of the size classes as described above and as indicated in Table 1, for instance. For instance, the cannula may be sized in accordance to size class VII or, alternatively, in accordance with any other of size classes I to VI.

FIGS. 4A and 4B show a cross-sections of cannula 400 along the corresponding dashed line indicated in FIG. 4. The pressure sensors 441, 442, and 443 may be, for example, fiber optical pressure sensors or MEMs sensors. As depicted in FIGS. 4A and 4B, each of the pressure sensors 441, 442, and 443 is connected to a signal line 444, 445, 446 which extends, from the respective sensor and embedded into the wall of the elongate body 410, proximally towards the proximal end 420 of the elongate body 410 and extends, as seen on FIGS. 4 and 5, proximally out of the elongate body 410, to transmit (e.g. electrical or optical) pressure signals from the respective pressure sensor 441, 442, or 443 to a pump controller, for instance.

Figure 5:
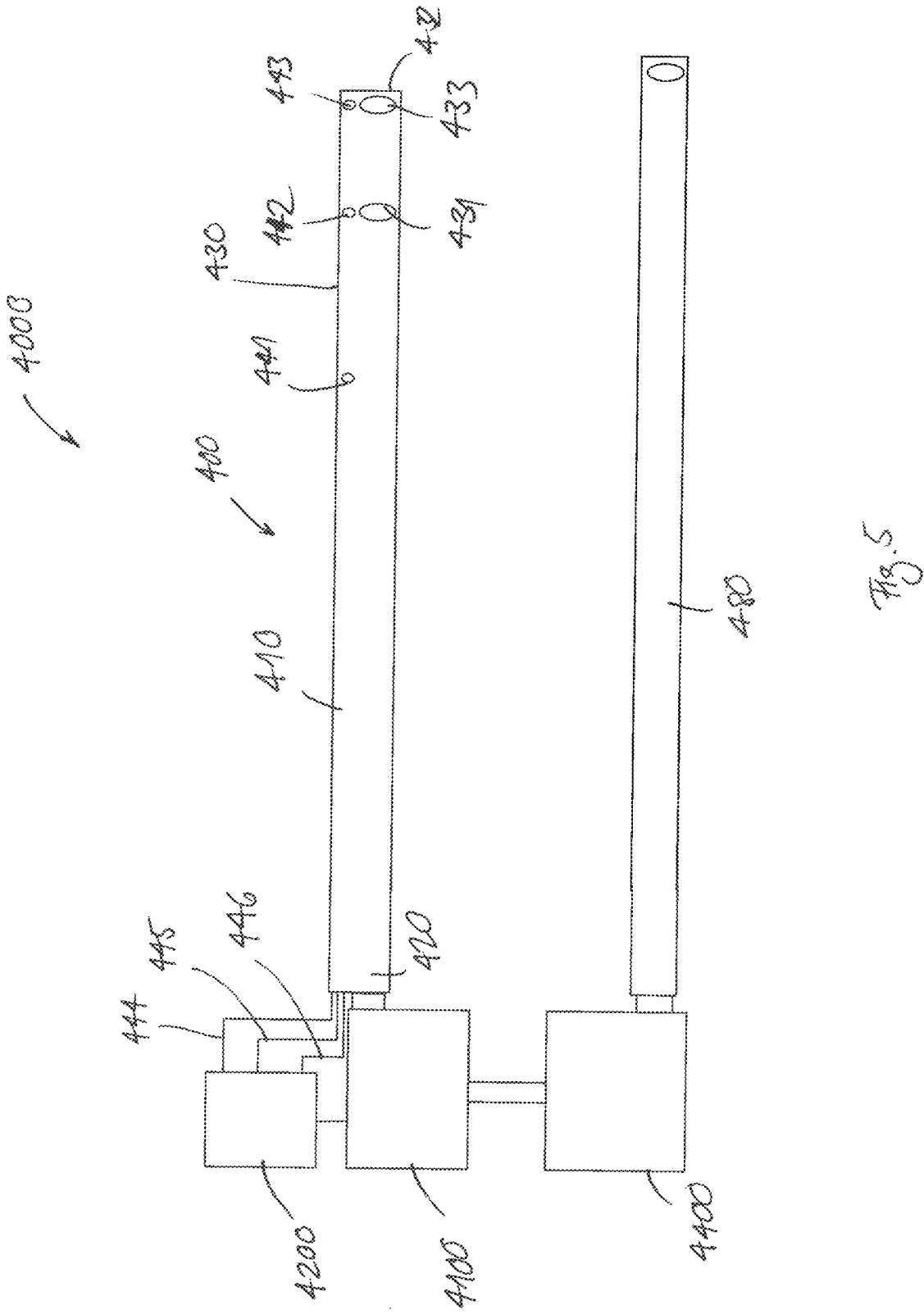

FIG. 5 shows an example of a mechanical circulatory support system 4000 in accordance with aspects of the present invention. The system 4000 is configured for providing mechanical circulatory support in accordance with the methods described herein and as described, for instance, with reference to FIG. 1 above. The system 4000 may include, for instance, the cardiac drainage cannula 400 shown in FIGS. 4, 4A and 4B for draining blood from a heart as described herein. The system 4000 may further include an extracorporeal blood pump 4100 connected to the drainage cannula 400 and, via an extracorporeal oxygenation device 4400 of the system 4000, to a perfusion cannula 480. The system 4000 further includes a pump controller 4200 connected to the blood pump 4100 and, via signal lines 444, 445, 446 to pressure sensors 441, 442, 443 of the cannula 400. The pressure sensors 441, 442, 443, are configured to measure the aforementioned blood pressures $P_1$, $P_2$, and $P_3$, respectively, and produce corresponding signals indicative of or including information about the measured blood pressures. The pump controller 4100 is configured to receive the pressure signals via signal lines 444, 445, 446 from each of the pressure sensors 441, 442, 443 to determine measured blood pressure values on the basis of the signals, and to control the blood pump 4100 on the basis of the received signals. The pump controller 4100 may be configured to automatically trend the measured blood pressures and/or compare the measured blood pressure with corresponding threshold values, for instance, as has described herein. For instance, the pump controller 4200 may be configured to adjust one or more pump parameters of the blood pump 4100, such as pump speed or pump rate, on the basis of the measured blood pressures.

FIG. 6 shows a further embodiment of a cardiac drainage cannula 600 in accordance with the invention. The cannula 600 includes an elongate body 460 including a proximal end portion 620, a distal end portion 630 and a main drainage lumen 634. The elongate body 610 further includes a left atrial drainage inlet 631 and a left ventricular drainage inlet 632 at the distal end portion 630 which are in fluid communication with the drainage lumen 634. A proximal drainage outlet 635 of the drainage lumen 634 is located at the proximal end portion 620 of the cannula body 610.

In the cannula 600 further comprises a right atrial pressure sensor 641 integrated into a wall of the elongate body 610, as illustrated in the cross-sectional view shown in FIG. 6A along the corresponding dashed line in FIG. 6. During use, the left atrial pressure sensor 641 is located within the right atrium 23 for measuring pressure $P_1$, a second left atrial pressure sensor 642 is integrated into the wall of the distal end portion 630 of the cannula 600. During use, left atrial pressure sensor 642 is located within the left atrium 20 for measuring pressure $P_2$. A third left ventricular pressure sensor 643 is integrated into the wall of the distal end portion 630 of the cannula 600. During use, left ventricular pressure sensor 643 is located within the left ventricle 22 for measuring pressure $P_3$. In alternative embodiments, only one or two of the three pressure sensors 641, 642, 643 may be present, for instance, only pressure sensors 641 and 642 for measuring only $P_1$ and $P_2$, or only pressure sensors 641 and 643 for measuring only $P_1$ and $P_3$, or only pressure sensors 642 and 643 for measuring only $P_2$ and $P_3$. As in case of the pressure sensors 141, 142, 143 of the cannula shown in FIG. 1, the measurements of the pressures $P_1$, $P_2$, and/or $P_3$ may be performed continuously and concurrently.

The cannula 600 may be sized to have dimension B to G (dimensions omitted in FIG. 6) in accordance with one of the size classes as described above and as indicated in Table 1, for instance. For instance, the cannula may be sized in accordance with size class II or, alternatively, in accordance with any other of size classes I and III to VII.

FIGS. 6A and 6B show a cross-sections of cannula 600 along the corresponding dashed line indicated in FIG. 6. The pressure sensors 641, 642, and 643 may be, for example, fiber optical pressure sensors or MEMs sensors and, optionally, may be configured to wirelessly transmit pressure signals, e.g. by emitting electromagnetic pressure signals such as high frequency signals, from the respective pressure sensor 641, 642, or 643 which may be wirelessly be received by a corresponding wireless signal receiver of a pump controller, for instance.

FIG. 7 shows an example of a mechanical circulatory support system 6000 in accordance with aspects of the present invention. The system 6000 is configured for providing mechanical circulatory support in accordance with the methods described herein and as described, for instance, with reference to FIG. 1 above. The system 6000 may include, for instance, the cardiac drainage cannula 600 shown in FIGS. 6, 6A and 6B for draining blood from a heart as described herein. The system 6000 may further include an extracorporeal blood pump 6100 connected to the drainage cannula 600 and, via an extracorporeal oxygenation device 6400 of the system 6000, to a perfusion cannula 680. The system 6000 further includes a pump controller 6200 connected to the blood pump 6100. Pump controller 6200 includes a wireless signal receiver 6210 configured to wireless receive pressure signal emitted by pressure sensors 641, 642, 643 of the cannula 600. The pressure sensors 641, 642, 643, are configured to measure the aforementioned blood pressures $P_1$, $P_2$, and $P_3$, respectively, and produce corresponding signals indicative of or including information about the measured blood pressures. The pump controller 6100 is configured to receive the pressure signals via signal lines 644, 645, 646 from each of the pressure sensors 641, 642, 643 to determine measured blood pressure values on the basis of the signals, and to control the blood pump 6100 on the basis of the received signals. The pump controller 6100 may be configured to automatically trend the measured blood pressures and/or compare the measured blood pressure with corresponding threshold values, for instance, as has described herein. For instance, the pump controller 6200 may be configured to adjust one or more pump parameters of the blood pump 6100, such as pump speed or pump rate, on the basis of the measured blood pressures.

The subject-matter of the disclosure may also relate, among others, to the following aspects:

A first aspect relates to a method of placing a cannula within a left atrium of a heart in a living body, comprising the steps of: (a) inserting the cannula percutaneously into an internal jugular vein of the body, (b) advancing the cannula through the internal jugular vein and into the right atrium of the heart, and (c) advancing the cannula through the atrial septum into the left atrium of the heart.

A second aspect relates to the method according to aspect 1, wherein the step (c) further comprises advancing the cannula from the left atrium through the mitral valve of the heart into the left ventricle of the heart.

A third aspect relates to the method of any one of the preceding aspects, comprising the step of: forming a percutaneous puncture by means of a needle, including puncturing the skin with the needle and advancing the needle through the skin and towards the internal jugular vein, and puncturing a wall of the internal jugular vein.

A fourth aspect relates to the method of any one of the preceding aspects, comprising the step of: puncturing the atrial septum using a sharp instrument to form a transseptal puncture, wherein step (c) includes advancing the cannula through the transseptal puncture of the atrial septum.

A fifth aspect relates to the method of any one of the preceding aspects, further comprising the step of: fixating the cannula to a skin portion adjacent to a percutaneous insertion site of the cannula.

A sixth aspect relates to the method of aspect 5, wherein the step of fixating the cannula to the skin portion adjacent to the percutaneous insertion site of the cannula includes forming a suture connecting the cannula to the skin portion.

A seventh aspect relates to a method of draining blood from a heart in a living body, the method comprising the steps of: (a) inserting a cannula percutaneously into an internal jugular vein of the body, (b) advancing the cannula through the internal jugular vein and into the right atrium of the heart, (c) advancing the cannula through the atrial septum into the left atrium of the heart, placing a distal end portion of the cannula at least partially within the left atrium, (d) intaking blood with the distal end portion of the cannula being placed at least partially within the left atrium of the heart and conducting the blood through the cannula from the distal end portion of the cannula to a proximal end portion of the cannula.

An eighth aspect relates to the method of aspect 7, wherein step (d) comprises: draining blood from the left atrium through at least one inlet of the cannula being placed within the left atrium.

A ninth aspect relates to the method of any one of aspects 7 or 8, wherein the step (c) further comprises: advancing the cannula from the left atrium through the mitral valve into the left ventricle of the heart, placing the distal end portion of the cannula partially within the left atrium and placing a distal end of the distal end portion of the cannula within the left ventricle.

A tenth aspect relates to the method of any one of aspects 7 to 9, wherein step (d) comprises: draining blood from the left atrium through at least one inlet of the cannula being placed within the left atrium and/or draining blood from the left ventricle through at least one further inlet of the cannula being placed within the left ventricle.

An eleventh aspect relates to the method of any one of aspects 7 to 10, wherein the proximal end portion of the cannula is connected to a blood pump located external to the body.

A twelfth aspect relates to the method of any one of aspects 7 to 11, further comprising utilizing at least one pressure sensor to measure at least one of: a first pressure $P_1$ indicative of blood pressure within the right atrium, a second pressure $P_2$ indicative of blood pressure within the left atrium, and/or a third pressure $P_3$ indicative of blood pressure within the left ventricle.

A thirteenth aspect relates to the method of aspect 12, wherein the at least one pressure sensor comprises at least one of: at least one pressure sensor permanently or removably fixed to the cannula and located within the right atrium, at least one pressure sensor permanently or removably fixed to the distal end portion of the cannula and located within the left atrium, at least one pressure sensor permanently or removably fixed to the distal end portion of the cannula and located within the left ventricle.

A fourteenth aspect relates to the method of any one of aspects 12 or 13, wherein the at least one pressure sensor comprises: at least one external pressure sensor located external to the body, wherein the cannula includes at least one pressure line, the at least one pressure line including at least one inlet located at or proximally to the distal end portion of the cannula, at least one outlet located at the proximal end portion of the cannula, and at least one lumen fluidly connecting the at least one inlet with the at least one outlet of the at least one pressure line, wherein at least one of the at least on inlet is located within a location selected from within the right atrium, within the left atrium and/or within the left ventricle, wherein the external pressure sensor is used to measure a pressure of blood being percutaneously drained from the right atrium, from the left atrium and/or from the left ventricle through the at least one pressure line of the cannula.

A fifteenth aspect relates to the method of any one of aspects 11 to 14, comprising controlling the external blood pump by means of a controller utilizing the at least one measured blood pressure.

A sixteenth aspect relates to the method of aspects 11 to 15, wherein controlling the external blood pump includes utilizing the at least one measured blood pressure to determine at least one of: a degree or an amount of right ventricular unloading; a precursor or an onset of right ventricular failure; a degree or an amount of left ventricular unloading; or a precursor or an onset of left ventricular failure.

A seventeenth aspect relates to the method of any one of aspects 7 to 16, wherein the blood is being percutaneously drained from the heart at a flow rate corresponding to 60% to 80% of a cardiac output of the heart.

An eighteenth aspect relates to the method of any one of aspects 7 to 17, further comprising the step of (e) percutaneously draining the blood out of the body and returning the percutaneously drained blood into the body by percutaneously infusing the blood into a vein and/or into an artery of the body.

A nineteenth aspect relates to the method of aspect 18, further comprising the step of: passing the percutaneously drained blood through an extracorporeal membrane oxygenation (ECMO) device.

A twentieth aspect relates to a cardiac drainage cannula for draining blood from a heart, the cardiac drainage cannula comprising an elongate body including a proximal end portion, a distal end portion, and at least one lumen extending through the elongate body from the distal end portion to the proximal end portion, the cannula comprising at least one inlet at the distal end portion of the elongate body and at least one proximal outlet at the proximal end portion of the elongate body, the at least one inlet being in fluid communication with the at least one outlet via the at least one lumen.

A twenty-first aspect relates to the cardiac drainage cannula of aspect 20, wherein an outer diameter of the elongate body is in a range of 4 mm to 11 mm.

A twenty-second aspect relates to the cardiac drainage cannula of any one of aspects 20 or 21, wherein the length of the elongate body is in a range of 16 cm to 52 cm.

A twenty-third aspect relates to the cardiac drainage cannula of any one of aspects 20 to 22, wherein the length of the elongated body is in a range of 16 cm to 52 cm.

A twenty-fourth aspect relates to the cardiac drainage cannula of any one of aspects 20 to 22, wherein the at least one inlet includes: a left ventricular drainage inlet located at a distal tip of the elongate body and a left atrial drainage inlet located proximal to the left ventricular drainage inlet.

A twenty-fifth aspect relates to the cardiac drainage cannula of aspect 24, wherein a distance between the left ventricular drainage inlet and the left atrial drainage inlet is in a range of 2 cm to 8 cm.

A twenty-sixth aspect relates to the cardiac drainage cannula of any one of aspects 24 or 25, wherein the at least one lumen of the elongate body includes a main drainage lumen, wherein the left ventricular drainage inlet and the left atrial drainage are in fluid communication with the main drainage lumen of the elongate body.

A twenty-seventh aspect relates to the cardiac drainage cannula of any one of aspects 20 to 26, further comprising at least one pressure sensor.

A twenty-eighth aspect relates to the cardiac drainage cannula of aspect 27, wherein the at least one pressure sensor comprises at least one of: a right atrial pressure sensor permanently or removably fixed to the elongate body and configured to measure blood pressure within the right atrium of a heart, a left atrial pressure sensor permanently or removably fixed to the distal end portion of the elongate body and configured to measure blood pressure within the left atrium of a heart, and/or a left ventricular pressure sensor permanently or removably fixed to the distal end portion of the elongate body and configured to measure blood pressure within the left ventricle of a heart.

A twenty-ninth aspect relates to the cardiac drainage cannula of aspect 28, wherein the right atrial pressure sensor is located proximal to the distal tip of the elongate member, wherein a distance between the right atrial pressure sensor and the distal tip is in range of 3 cm to 13 cm, the left atrial pressure sensor is located proximal to the distal tip of the elongate member, wherein a distance between the left atrial pressure sensor and the distal tip is in range of 2 cm to 8 cm, and/or wherein the left ventricular pressure sensor is located at the distal tip of the elongate body.

A thirtieth aspect relates to the cardiac drainage cannula of any one of aspects 28 or 29, wherein the right atrial pressure sensor is located proximal to the left atrial pressure sensor, wherein a distance between the right atrial pressure sensor and the left atrial pressure sensor in range of 1 cm to 5 cm.

A thirty-first aspect relates to the cardiac drainage cannula any of aspects 20 to 30, wherein the at least one lumen of the elongate body includes at least one of: a right atrial pressure line extending from a proximal outlet of the right atrial pressure line at the proximal end portion of the elongate body to a right atrial inlet of the right atrial pressure line located at the distal end portion of the elongate body, a left atrial pressure line extending from a proximal outlet of the left atrial pressure line at the proximal end portion of the elongate body to a left atrial inlet of the left atrial pressure line located at the distal end portion of the elongate body, and/or a left ventricular pressure line extending from a proximal outlet of the left ventricular pressure line at the proximal end portion of the elongate body to a left ventricular inlet of the left atrial pressure line located at the distal tip of the elongate body.

A thirty-second aspect relates to the cardiac drainage cannula of aspect 31, wherein the right atrial pressure inlet is located proximal to the distal tip of the elongate member, wherein a distance between the right atrial pressure inlet and the distal tip is in range of 3 cm to 13 cm, the left atrial pressure inlet is located proximal to the distal tip of the elongate member, wherein a distance between the left atrial pressure inlet and the distal tip is in range of 2 cm to 8 cm.

A thirty-third aspect relates to the cardiac drainage cannula of one of aspects 30 to 32, wherein the right atrial pressure inlet is located proximal to the left atrial pressure inlet, wherein a distance between the right atrial pressure inlet and the left atrial pressure inlet in range of 1 cm to 5 cm.

A thirty-fourth aspect relates to the cardiac drainage cannula of any one of aspects 19 to 33, further comprising a securing means for securing the proximal end portion of the elongated body of the cannula to a skin portion adjacent to a percutaneous insertion site of the cannula.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

LIST OF REFERENCE SIGNS 10 heart
20 left atrium
22 left ventricle
23 right atrium
24 atrial septum
25 mitral valve
26 transseptal puncture
31 internal jugular vein
32 brachiocephalic vein
33 superior vena cava
34 subclavian artery
60 skin
62 puncture
100; 200; 400; 600 cannula
110; 210; 410; 610 elongate body
120; 220; 420; 620 proximal end portion
130; 230; 430; 630 distal end portion
131; 231; 431; 631 left atrial drainage inlet
132; 232; 432; 632 distal tip
133; 233; 433; 633 left ventricular drainage inlet
234; 434; 634 drainage lumen
135; 235; 435; 635 proximal drainage outlet
141; 441; 641 right atrial pressure sensor (for measuring $P_1$)

142; 442; 642 left atrial pressure sensor (for measuring $P_2$)
143; 443; 643 left ventricular pressure sensor (for measuring $P_3$)
444, 445, 446 signal line of pressure sensor
244 right atrial pressure inlet (measuring $P_1$)
245 left atrial pressure inlet (measuring $P_2$)
246 left ventricular pressure inlet (measuring $P_3$)
247 right atrial pressure lumen (measuring $P_1$)
248 left atrial pressure lumen (measuring $P_2$)
249 left ventricular pressure lumen (measuring $P_3$)
150 securing means
151 fixation member
152 hole
153 suture thread
180; 280; 480; 680 perfusion cannula
2000; 4000; 6000 system
2100; 4100; 6100 blood pump
2200; 4200; 6200 blood pump controller
6210 wireless signal receiver
2310; 2320; 2330 external pressure sensor
2400; 4400; 6400 oxygenator

The invention claimed is:

1. A method of draining blood from a heart in a living body, comprising:
   (a) inserting a cannula percutaneously into an internal jugular vein of the body,
   the cannula including at least one left ventricular drainage inlet at a distal portion of the cannula, at least one left atrial drainage inlet proximal of the a left ventricular drainage inlet, and at least one proximal outlet at a proximal portion of the cannula, wherein the at least one left ventricular drainage inlet, the at least one left atrial drainage inlet and the at least one proximal outlet are in fluid communication with a single drainage lumen of the cannula extending from the distal portion of the cannula to the proximal portion of the cannula;
   (b) advancing the cannula through the internal jugular vein and into a right atrium of the heart;
   (c) advancing the cannula through an atrial septum into a left atrium of the heart and from the left atrium through a mitral valve of the heart into a left ventricle of the heart;
   (d) intaking blood through the at least one left atrial drainage inlet of the cannula being placed within the left atrium of the heart into the single drainage lumen of the cannula, simultaneously intaking blood through the at least one left ventricular drainage inlet of the cannula being placed within the left ventricle of the heart into the single drainage lumen of the cannula, and conducting the blood from the left atrium and the left ventricle through the single drainage lumen of the cannula to the proximal portion of the cannula to simultaneously drain blood from the left atrium and the left ventricle; and
   (e) percutaneously draining the blood out of the body through the at least one proximal outlet of the cannula and returning the percutaneously drained blood into the body by percutaneously infusing the blood into a vein and/or into an artery of the body.

2. The method of claim 1, further comprising:
   forming a percutaneous puncture by means of a needle, including puncturing the skin with the needle and advancing the needle through the skin and towards the internal jugular vein, and puncturing a wall of the internal jugular vein.

3. The method of claim 1, further comprising:
   puncturing the atrial septum using a sharp instrument to form a transseptal puncture, wherein step (c) includes advancing the cannula through the transseptal puncture of the atrial septum.

4. The method of claim 1, further comprising:
   fixating the cannula to a skin portion adjacent to a percutaneous insertion site of the cannula.

5. The method of claim 4, wherein the fixating the cannula to the skin portion adjacent to the percutaneous insertion site of the cannula includes forming a suture connecting the cannula to the skin portion.

6. A method of draining blood from a heart in a living body, the method comprising:
   (a) inserting a cannula percutaneously into an internal jugular vein of the body;
   (b) advancing the cannula through the internal jugular vein and into a right atrium of the heart;
   (c) advancing the cannula through an atrial septum into a left atrium of the heart and advancing the cannula from the left atrium through a mitral valve into a left ventricle of the heart, thereby placing a distal end portion of the cannula partially within the left atrium and a distal end of the distal end portion of the cannula within the left ventricle;
   (d) intaking blood through at least one inlet of the cannula being placed within the left atrium of the heart to drain blood from the left atrium and/or intaking blood through at least one further inlet of the cannula being placed within the left ventricle to drain blood from the left ventricle, wherein the at least one inlet includes a left atrial drainage inlet located proximal to a left ventricular drainage inlet, and wherein the at least one further inlet includes the left ventricular drainage inlet located at a distal tip of the cannula, wherein the cannula includes a single drainage lumen, the left ventricular drainage inlet and the left atrial drainage inlet being in fluid communication with the single drainage lumen, conducting the blood through the cannula from the distal end portion of the cannula to a proximal end portion of the cannula;
   (e) draining blood from the left ventricle through the ventricular drainage inlet into the single drainage lumen and draining blood from the left atrium through the left atrial drainage inlet into the single drainage lumen; and
   (f) conducting the blood drained from the left atrium and the left ventricle proximally through the single drainage lumen percutaneously out of the body; and
   (g) percutaneously draining the blood out of the body and returning the percutaneously drained blood into the body by percutaneously infusing the blood into a vein and/or into an artery of the body.

7. The method of claim 6, wherein step (d) comprises:
   draining blood from the left atrium through at least one inlet of the cannula being placed within the left atrium.

8. The method of claim 6, wherein the proximal end portion of the cannula is connected to a blood pump located external to the body.

9. The method of claim 8, comprising controlling the external blood pump by means of a controller utilizing at least one measured blood pressure.

10. The method of claim 9, wherein controlling the external blood pump includes utilizing the at least one measured blood pressure to determine at least one of:
    a degree or an amount of right ventricular unloading;
    a precursor or an onset of right ventricular failure;

a degree or an amount of left ventricular unloading; or
a precursor or an onset of left ventricular failure.

11. The method of claim 9, further comprising controlling the external blood pump with a controller based on a degree or an amount of right ventricular unloading determined from the at least one measured blood pressure.

12. The method of claim 9, further comprising controlling the external blood pump with a controller based on a precursor or an onset of right ventricular failure determined from the at least one measured blood pressure.

13. The method of claim 9, further comprising controlling the external blood pump with a controller based on a degree or an amount of left ventricular unloading determined from the at least one measured blood pressure.

14. The method of claim 9, further comprising controlling the external blood pump with a controller based on a precursor or an onset of left ventricular failure determined from the at least one measured blood pressure.

15. The method of claim 8, wherein the blood is being percutaneously drained from the heart at a flow rate corresponding to 60% to 80% of a cardiac output of the heart.

16. The method of claim 6, further comprising utilizing at least one pressure sensor to measure at least one of:
a first pressure $P_1$ indicative of blood pressure within the right atrium,
a second pressure $P_2$ indicative of blood pressure within the left atrium, and/or
a third pressure $P_3$ indicative of blood pressure within the left ventricle.

17. The method of claim 16, wherein the at least one pressure sensor comprises at least one of:
at least one pressure sensor permanently or removably fixed to the cannula and located within the right atrium,
at least one pressure sensor permanently or removably fixed to the distal end portion of the cannula and located within the left atrium,
at least one pressure sensor permanently or removably fixed to the distal end portion of the cannula and located within the left ventricle.

18. The method of claim 16, wherein the at least one pressure sensor comprises:
at least one external pressure sensor located external to the body, wherein the cannula includes at least one pressure line, the at least one pressure line including at least one inlet located at or proximally to the distal end portion of the cannula, at least one outlet located at the proximal end portion of the cannula, and at least one lumen fluidly connecting the at least one inlet with the at least one outlet of the at least one pressure line, wherein at least one of the at least on inlet is located within a location selected from within the right atrium, within the left atrium and/or within the left ventricle, wherein the external pressure sensor is used to measure a pressure of blood being percutaneously drained from the right atrium, from the left atrium and/or from the left ventricle through the at least one pressure line of the cannula.

19. The method of claim 16, further comprising comparing the first pressure P1 with a first threshold and generating an alert indicating right ventricular failure when the first pressure P1 is greater than the first threshold.

20. The method of claim 19, wherein the first threshold is 10 mmHg.

21. The method of claim 16, further comprising comparing the second pressure P2 with a second threshold and generating an alert indicating right ventricular failure when the second pressure P2 is greater than the second threshold.

22. The method of claim 21, wherein the second threshold is 15 mmHg or 20 mmHg.

23. The method of claim 16, further comprising comparing the third pressure P3 with a third threshold and generating an alert indicating left ventricular failure when the third pressure P3 is greater than the third threshold.

24. The method of claim 23, wherein the third threshold is 15 mmHg.

25. The method of claim 6, further comprising the step of:
passing the percutaneously drained blood through an extracorporeal membrane oxygenation (ECMO) device.

* * * * *